(12) United States Patent
Pouchoulin et al.

(10) Patent No.: US 12,318,520 B2
(45) Date of Patent: Jun. 3, 2025

(54) CONTAINER FOR FLUIDS AND APPARATUS FOR TEMPERATURE CONTROL, E.G. WARMING, OF MEDICAL FLUIDS

(71) Applicant: GAMBRO LUNDIA AB, Lund (SE)

(72) Inventors: Dominique Pouchoulin, Tramoyes (FR); Eugen Nisipeanu, Wadsworth, IL (US)

(73) Assignee: Gambro Lundia AB, Lund (SE)

( * ) Notice: Subject to any disclaimer, the term of this patent is extended or adjusted under 35 U.S.C. 154(b) by 0 days.

(21) Appl. No.: 18/380,360

(22) Filed: Oct. 16, 2023

(65) Prior Publication Data

US 2024/0042111 A1  Feb. 8, 2024

Related U.S. Application Data

(63) Continuation of application No. 16/611,525, filed as application No. PCT/EP2018/062135 on May 9, 2018, now Pat. No. 11,786,646.

(30) Foreign Application Priority Data

May 11, 2017  (EP) .................................... 17170551

(51) Int. Cl.
  *A61M 1/16*  (2006.01)
  *A61B 90/00*  (2016.01)
  (Continued)

(52) U.S. Cl.
  CPC ........ *A61M 1/1668* (2014.02); *A61M 1/1623* (2014.02); *A61M 1/166* (2014.02);
  (Continued)

(58) Field of Classification Search
  None
  See application file for complete search history.

(56) References Cited

U.S. PATENT DOCUMENTS

| 4,731,072 A | * | 3/1988 | Aid | ....................... A61F 7/0085 |
| | | | | 604/408 |
| 6,539,172 B2 | * | 3/2003 | Akahane | ................. F24H 1/121 |
| | | | | 604/6.13 |

(Continued)

FOREIGN PATENT DOCUMENTS

| DE | 102015113325 | 2/2017 |
| GB | 2101966 A | 1/1983 |

(Continued)

OTHER PUBLICATIONS

Extended European Search Report; European Application No. 17170551.0-1651; dated Nov. 11, 2017; 9 pages.

(Continued)

*Primary Examiner* — Jonathan M Peo
(74) *Attorney, Agent, or Firm* — K&L Gates LLP

(57) ABSTRACT

A container for warming fluids comprises an inlet port, an outlet port, a fluid conduit configured for fluidly communicating the inlet and outlet ports, and deflection sections. The fluid conduit has a non-constant maximum width in a direction of fluid flow through the fluid conduit. The deflection sections further comprise an entry section and an exit section, each respective exit section being arranged downstream, in the direction of fluid flow, from each respective entry section. The maximum width of the fluid conduit decreases along the direction of fluid flow through the entry section over a first distance and the maximum width of the fluid conduit increases along the direction of fluid flow through the exit section over a second, different distance. A blood treatment apparatus including the above-described container is also provided.

22 Claims, 10 Drawing Sheets

(51) Int. Cl.
*A61F 7/00* (2006.01)
*A61M 1/30* (2006.01)
*A61M 1/36* (2006.01)
*F28F 13/08* (2006.01)

(52) U.S. Cl.
CPC .......... *A61M 1/308* (2014.02); *A61M 1/3623* (2022.05); *F28F 13/08* (2013.01); *A61B 2090/0808* (2016.02); *A61F 2007/0059* (2013.01); *A61M 2205/0216* (2013.01); *A61M 2206/10* (2013.01)

(56) References Cited

U.S. PATENT DOCUMENTS

| 2005/0055074 | A1* | 3/2005 | Tak ........................ A61M 5/44 607/104 |
| 2006/0000829 | A1 | 1/2006 | Furnrohr et al. |
| 2008/0262409 | A1 | 10/2008 | Derrico et al. |
| 2009/0012655 | A1* | 1/2009 | Kienman ............ A61M 1/1605 219/50 |
| 2014/0216994 | A1 | 8/2014 | Ki |

FOREIGN PATENT DOCUMENTS

| GB | 2117101 A | 10/1983 | |
| JP | 2006034515 | 2/2006 | |
| JP | 2017023441 | 2/2017 | |
| KR | 870001592 | 3/1987 | |
| WO | WO-2015120843 A1 * | 8/2015 | ............. A61M 5/44 |
| WO | 2016041745 | 3/2016 | |

OTHER PUBLICATIONS

International Search Report; International Application No. PCT/EP2018/062135; mailed Jul. 30, 2018; 4 Pages.
Written Opinion of the International Searching Authority; International Application No. PCT/EP2018/062135; mailed Jul. 30, 2018; 7 Pages.
Korean Office Action—Appln No. 10-2019-7036570 dated Dec. 26, 2022—27 pages.
1st Chinese Office Action dated Dec. 3, 2021, issued by the CNPTO for corresponding Chinese Patent Application No. 2018800312387; 16 Pages.
Chinese Search Report dated Nov. 29, 2021; issued by the CNPTO for corresponding Chinese Patent Application No. 2018800312387; 3 Pages.
First Office Action; Japanese Application No. 2019-560754; Notice of Reasons for Refusal dated Jan. 31, 2022 dated Jan. 31, 2022.
First Examination Report; Indian National Phase Application No. 20191704479; dated Feb. 28, 2022.

* cited by examiner

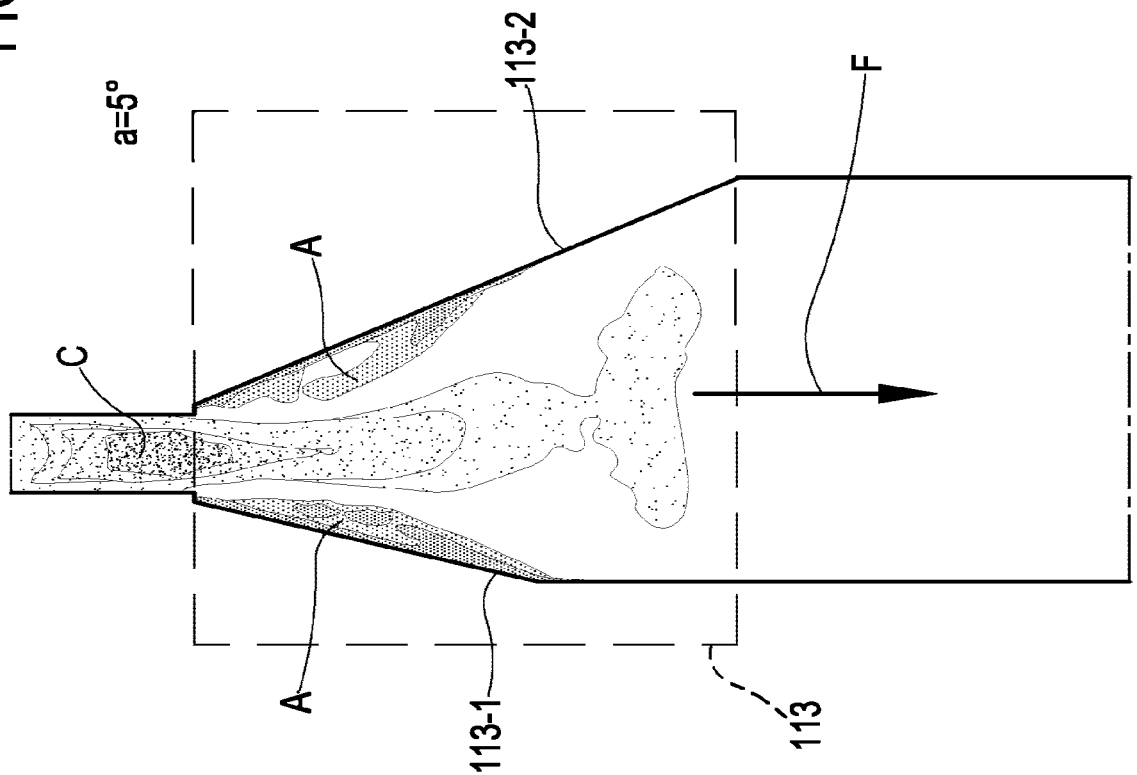
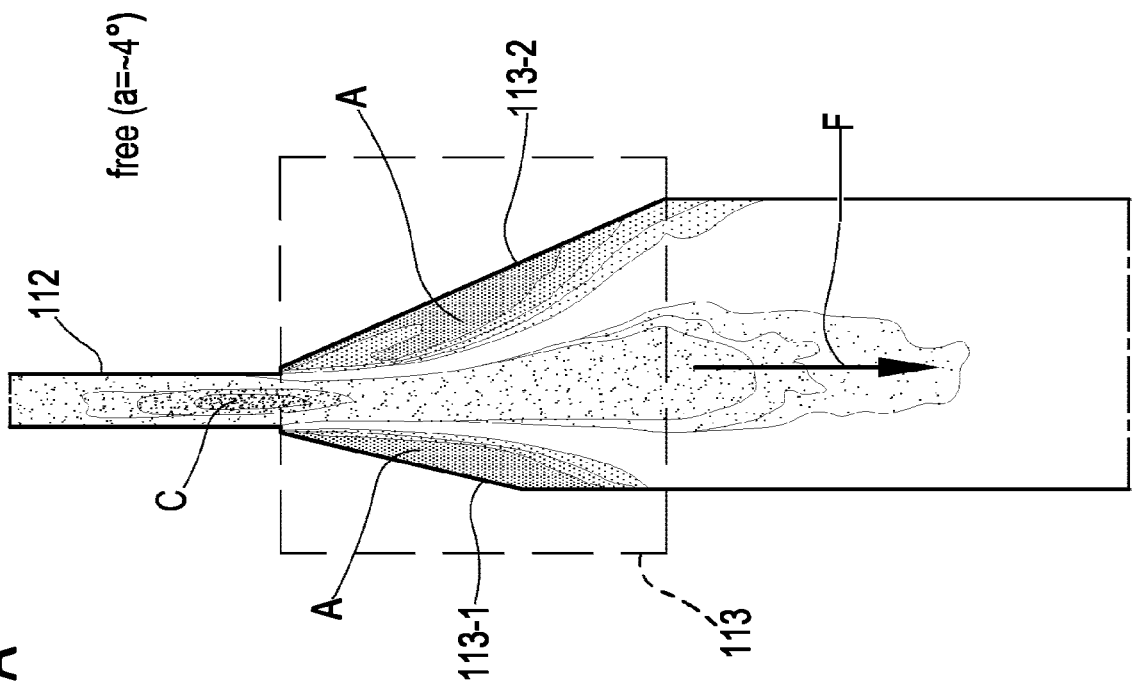

CONTAINER FOR FLUIDS AND APPARATUS FOR TEMPERATURE CONTROL, E.G. WARMING, OF MEDICAL FLUIDS

PRIORITY CLAIM

The present application is a continuation application of U.S. application Ser. No. 16/611,525, filed Nov. 7, 2019, now U.S. Pat. No. 11,786,646, which is a National Phase of International Application No. PCT/EP2018/062135, filed May 9, 2018, published as PCT Publication No. WO 2018/206718 on Nov. 15, 2018, which claims priority to EP Application No. 17170551.0, filed May 11, 2017, the entire contents of each of which are incorporated herein by reference and relied upon.

TECHNICAL FIELD

The present invention relates to a container for fluids (in particular, but not exclusively, a container for cooling or warming fluids) and to an apparatus for temperature control, e.g. warming or cooling, fluids in an apparatus for extracorporeal blood treatment.

The apparatus for extracorporeal blood treatment includes an apparatus for fluid temperature control (warming or cooling) that is configured to regulate the temperature of medical fluids, for example blood, in combination with a bag for warming or cooling medical fluids. The bag is inserted into the fluid temperature control apparatus and the temperature is regulated, for example, by heat being transferred (or removed) from a heating area of the fluids temperature control apparatus through the material of the bag and into (or form) the medical fluid flowing through the bag.

The method for controlling the extracorporeal blood treatment apparatus includes controlling the temperature of a medical fluid, for example blood, using the fluid temperature control apparatus and a bag.

BACKGROUND

In medical applications such as extracorporeal blood treatment it is often desired to regulate the temperature of medical fluids, for example in cases where the individual temperature of a medical fluid is important for particular chemical or biological reactions to take place, or for treatment to be performed under optimal conditions. Other cases include returning blood to a patient that has been withdrawn for extracorporeal treatment (e.g. dialysis, hemofiltration, hemodiafiltration).

In many cases, the flow rate of medical fluid varies over time and depends on a number of factors including treatment type, patient properties and condition, topology of the extracorporeal circuit, etc. Regulating the temperature under these varying conditions requires a robust system facilitating reliable treatment and handling of medical fluids.

U.S. Pat. No. 6,464,666 discloses a fluid warming cassette with a stiffening frame structure and an integral handle supporting a parenteral fluid container. The fluid container is desirably thin to minimize heat exchange inefficiencies. The frame structure permits the thin fluid container to be inserted into the narrow space between fixed position warming plates of a warming unit. The frame structure has a quadrilateral shape with sides and ends. The fluid container is attached, at its periphery to the sides and ends of the frame structure, within the quadrilateral shape. Part of the frame structure is formed into a handle to assist in both the insertion and removal of the cassette from a warming unit.

U.S. 2008/0262409 discloses a system and method for manufacturing a heat exchanger. The heat exchanger comprises a casing with a serpentine pathway, a membrane enclosed by the casing, an inlet tube or valve for fluid to enter the heat exchanger, and an outlet tube or valve for fluid to exit the heat exchanger. The casing encloses the membrane, which resides between the casing and the fluid. The exterior casing possesses a wide asymmetrical serpentine pathway and particularly comprises a rigid, plastic frame. The frame consists of two halves, where the shape of the pathway is mirrored on both halves of the frame so that when the halves are sandwiched together they form a channel. The method comprises attaching a plurality of tubes or valves to a flexible container, creating an asymmetric passage in a rigid shell, enclosing the flexible container within the shell, and sealing the shell.

JP 2001120658 discloses a medical heat exchanger bag and method for manufacturing the same by which a liquid is prevented from leaking outside due to breakage caused by the internal pressure generated when the liquid flows in a liquid path, by reducing a load applied to the inside of a bent part of a medical heat exchanger bag. The bag is provided with a series of elongated channels and a series of bends that include two curved channels for fluid to flow through. Both the elongated and the curved channels have increasing or decreasing diameter along the direction of fluid flow.

Known designs bags or cassettes have shown problems with potential air retention in the internal conduit. Air retention may be caused to some extent by the presence of low speed areas in the internal conduit, for example at inlet/outlet sections, and at an outer border of the one or more bends typically included in the conduit. If the conveyed fluid is blood, then such effects entail the risk of blood clotting. Due to air retention and/or the risk of blood clotting, the operating times of known designs are often limited in order to ensure safe and reliable treatment.

Therefore, there is a need for providing an apparatus for warming fluids and a corresponding container for fluids that reduces or minimizes air retention and/or the risk of blood clotting in case blood is conveyed through the container.

SUMMARY

A general aim of the present invention is to provide an apparatus for controlling the temperature of fluids for use in an extracorporeal blood treatment apparatus that alleviates or minimizes the above-mentioned drawbacks.

It is a further aim of the present invention to provide a container suitable for use with an apparatus for controlling the temperature of (e.g., warming or cooling) fluids that alleviates or minimizes the above-mentioned drawbacks.

It is a further aim of the present invention to provide a container for use with an apparatus for controlling the temperature of (e.g., warming or cooling) fluids that minimizes air retention and/or the risk of blood clotting by preventing or minimizing the formation of low fluid flow areas in an internal conduit of the container.

It is a further aim of the present invention to provide a container for use with an apparatus for controlling the temperature of (e.g., warming or cooling) fluids that minimizes pressure drop and/or risk of hemolysis by preventing or minimizing the formation of high fluid flow areas in an internal conduit of the container.

It is a further aim of the present invention to provide a container for use with an apparatus for controlling the temperature of (e.g., warming or cooling)fluids that minimizes air retention and/or the risk of blood clotting especially at lower fluid flow rates through the container. This may also entail substantial advantages in applications in which fluids other than blood are conveyed through the container.

It is a further aim of the present invention to provide a container for use with an apparatus for warming fluids that minimizes the risk for formation of hot spots by preventing or minimizing the retention of air bubbles in an internal conduit of the container. This may also entail preventing damage to the fluid (e.g. hemolysis in the case of blood, degasing or chemical decomposition in other cases) and/or to the material the container is made of, for example, due to overheating.

It is a further aim of the present invention to provide a container for use with an apparatus for warming fluids that improves or maximizes heat transfer by preventing the formation of hot spots and/or by minimizing the retention of air bubbles. This may also entail improving or optimizing the heat exchange between heating surfaces to the apparatus and the fluid conveyed through the container.

It is a further aim of the present invention to provide a container for use with an apparatus for controlling the temperature of (e.g., warming or cooling) fluids that can be manufactured at the same or lower cost as known containers, while providing one or more of the above advantages.

At least one of the above-indicated aims is attained by a container and an apparatus according to one or more of the appended claims, taken singly or in any combination.

In a $1^{st}$ independent aspect there is provided a container for fluids, in particular a container for warming or cooling fluids, the container comprising an inlet port; an outlet port; and a fluid conduit configured for putting the inlet port in fluid communication with the outlet port and comprising one or more deflection sections. The fluid conduit has a non-constant maximum width in a direction of fluid flow F through the fluid conduit. At least one of the one or more deflection sections further comprises an entry section and an exit section, each respective exit section being arranged downstream, in the direction of fluid flow, from each respective entry section. The maximum width of the fluid conduit decreases along the direction of fluid flow through the entry section over a first distance $D_e$ and the maximum width of the fluid conduit increases along the direction of fluid flow through the exit section over a second distance $D_x$, the first distance and the second distance being different from one another.

In a $2^{nd}$ aspect according to the $1^{st}$ aspect, the direction of fluid flow F through the fluid conduit is based on a direction from the inlet port towards the outlet port.

In a $3^{rd}$ aspect according to anyone of the preceding aspects, the first distance $D_e$ is smaller than the second distance $D_x$.

In a $4^{th}$ aspect according to anyone of the preceding aspects, the maximum width of the fluid conduit decreases along the direction of fluid flow F through the entry section from a first width $L_c$ to a second width $L_t$.

In a $5^{th}$ aspect according to the preceding aspect, with $$0.5 \leq \frac{L_t}{L_c} \leq 0.85,$$

particularly with $$0.7 \leq \frac{L_t}{L_c} \leq 0.8,$$

more particularly with $$\frac{L_t}{L_c} = 0.75.$$

In a $6^{th}$ aspect according to anyone of the two preceding aspects, the maximum width of the fluid conduit increases along the direction of fluid flow F through the exit section from the second width $L_t$ to the first width $L_c$.

In a $7^{th}$ aspect according to anyone of the preceding aspects, the maximum width of the fluid conduit decreases non uniformly along the direction of fluid flow F through the entry section with at least a first phase and a second phase, the decrease in the first phase and the decrease in the second phases being different from one another.

In an $8^{th}$ aspect according to anyone of aspects 1 to 6, the maximum width of the fluid conduit decreases along the direction of fluid flow F through the entry section less than linearly in a first phase and more than linearly in a second phase.

In a $9^{th}$ aspect according to anyone of the two preceding aspects, the first phase covers at least 50% of the first distance $D_e$.

In a $10^{th}$ aspect according to anyone of the preceding aspects, the maximum width of the fluid conduit increases along the direction of fluid flow F through the exit section substantially constantly over the second distance $D_x$.

In an $11^{th}$ aspect according to anyone of the preceding aspects, the first distance $D_e$ is between about 0.3 times the maximum width and about 2.0 times the maximum width, particularly between about 0.5 times the maximum width and about 0.7 times the maximum width, more in detail about 0.6 times the maximum width.

In a $12^{th}$ aspect according to anyone of the preceding aspects, the second distance $D_x$ is between about 0.8 times the maximum width and about 4.0 times the maximum width, particularly between about 1.0 times the maximum width and about 2.0 times the maximum width.

In a $13^{th}$ aspect according to anyone of the preceding aspects, for each of the one or more deflection sections, the entry section has a first end and a second end, the first end of the entry section being upstream, in the direction of fluid flow F, of the second end of the entry section; and the exit section has a first end and a second end, the first end of the exit section being upstream, in the direction of fluid flow F, of the second end of the exit section.

In a $14^{th}$ aspect according to the preceding aspect, the maximum width of the fluid conduit at the first end of the entry section is substantially equal to the maximum width of the fluid conduit at the second end of the exit section.

In a $15^{th}$ aspect according to anyone of the two preceding aspects, the maximum width of the fluid conduit at the first end of the entry section is between about 18 mm and 22 mm, particularly between about 19 mm and about 21 mm, and/or the maximum width of the fluid conduit at the second end of the entry section is between about 13 mm and 17 mm, particularly between about 14 mm and about 16 mm.

In a $16^{th}$ aspect according to anyone of the three preceding aspects 1 to 14, the maximum width of the fluid conduit at the first end of the entry section is between about 38 mm and 42 mm, particularly between about 39 mm and about 41 mm, and/or the maximum width of the fluid conduit at the second end of the entry section is between about 28 mm and 32 mm, particularly between about 29 mm and about 31 mm.

In a 17th aspect according to anyone of the preceding aspects 13 to 15, the maximum width of the fluid conduit at the second end of the exit section is between about 18 mm and 22 mm, particularly between about 19 mm and about 21 mm, and/or the maximum width of the fluid conduit at the first end of the exit section is between about 13 mm and 17 mm, particularly between about 14 mm and about 16 mm.

In an 18th aspect according to anyone of the preceding aspects 13, 14, 16, the maximum width of the fluid conduit at the second end of the exit section is between about 38 mm and 42 mm, particularly between about 39 mm and about 41 mm, and/or the maximum width of the fluid conduit at the first end of the exit section is between about 28 mm and 32 mm, particularly between about 29 mm and about 31 mm.

In a 19th aspect according to anyone of the preceding aspects, each of the one or more deflection sections further comprises an intermediate section interposed between the entry section and the exit section.

In a 20th aspect according to the preceding aspect, each respective intermediate section has a substantially constant width.

In a 21st aspect according to anyone of aspects 4 to 6, in combination with the preceding aspect, the constant width is equal to the second width $L_t$.

In a 22nd aspect according to anyone of the three preceding aspects, each respective intermediate section is directly adjacent to the corresponding entry section, particularly the corresponding entry section being a direct extension of the respective intermediate section.

In a 23rd aspect according to anyone of the four preceding aspects, each respective intermediate section is directly adjacent to the corresponding exit section, particularly the corresponding exit section being a direct extension of the respective intermediate section.

In a 24th aspect according to anyone of the five preceding aspects, the intermediate section is provided with an inner radius $R_2$ calculated as $$R_2 = \left(1 - \frac{L_t}{L_c}\right) \cdot L_c + \frac{\text{weld}}{2},$$

with $L_c$=the maximum width, $L_t$=the width of the intermediate section (110i), and weld=width of weld; and/or the ratio $R_2/L_c$ between the inner radius ($R_2$) and the maximum width ($L_c$) ranges from 0.15 to 0.50, particularly from 0.2 to 0.3, and is more in particular equal to about 0.25.

In a 25th aspect according to anyone of the six preceding aspects, the intermediate section is provided with an outer radius $R_3$ calculated as $$R_3 = L_c + \frac{\text{weld}}{2},$$

with $L_c$=the maximum width, and weld=width of weld.

In a 26th aspect according to anyone of aspects 19 to 25, the intermediate section has an inner edge and an opposite outer edge, the inner edge having a radius smaller than a radius of the outer edge. Each of the entry section and the exit section has a respective inner edge in extension to the inner edge of the intermediate section. Each of the entry section and the exit section has a respective outer edge in extension to the outer edge of the intermediate section.

In a 27th aspect according to the preceding aspect, the maximum width of the fluid conduit decreases along the direction of fluid flow F through the entry section substantially due to a directional change of the inner edge of the entry section, optionally the outer edge of the entry section continuing substantially straight and/or tangentially in extension from the outer edge of the intermediate section.

In a 28th aspect according to anyone of the two preceding aspects, the maximum width of the fluid conduit increases along the direction of fluid flow F through the exit section substantially due to a directional change of the inner edge of the exit section, optionally the outer edge of the exit section continuing substantially straight and/or tangentially in extension from the outer edge of the intermediate section.

In a 29th aspect according to anyone of aspects 1 to 25, the maximum width of the fluid conduit decreases along the direction of fluid flow F through the entry section substantially due to a directional change of an inner edge of the entry section, and/or an outer edge of the entry section is substantially straight.

In a 30th aspect according to anyone of aspects 1 to 25 or 29, the maximum width of the fluid conduit increases along the direction of fluid flow F through the exit section substantially due to a directional change of an inner edge of the exit section, and/or an outer edge of the exit section is substantially straight.

In a 31st aspect according to anyone of the preceding aspects in combination with aspect 19, the intermediate section is provided with a deflection of at least about 90°, particularly about 180°.

In a 32nd aspect according to anyone of the preceding aspects, the fluid conduit further comprises a plurality of connection sections.

In a 33rd aspect according to the preceding aspect, the fluid conduit is provided, along each of the plurality of connection sections, with a substantially constant maximum width; and/or the fluid conduit is, along each of the plurality of connection sections, substantially straight.

In a 34th aspect according to anyone of the two preceding aspects, the fluid conduit is provided with a maximum width along one of the plurality of connection sections equal to a maximum width along each other of said plurality of connection sections.

In a 35th aspect according to anyone of the three preceding aspects, the plurality of connection sections comprises an inlet section connected to the inlet port and to an adjacent first connection section of the plurality of connection sections, the inlet section being configured to provide the fluid conduit with a transition from a diameter of the inlet port to a maximum width of the fluid conduit at the first connection section, particularly the inlet section including an inner edge and an outer edge, the inner edge and the outer edge each forming a respective inlet angle with respect to an axis of the inlet port of about 5° to about 30°, more particularly of less than about 15°.

In a 36th aspect according to anyone of the four preceding aspects, the plurality of connection sections comprises an outlet section connected to the outlet port and to an adjacent second connection section of the plurality of connection sections, the outlet section being configured to provide the fluid conduit with a transition from a diameter of the outlet port to a maximum width of the fluid conduit at the second connection section, particularly the outlet section including an inner edge and an outer edge, the inner edge and the outer edge each forming a respective outlet angle with respect to an axis of the outlet port of about 25° to about 60°, more particularly of less than about 40°.

In a 37th aspect according to anyone of the preceding aspects, the fluid conduit has a meandering or serpentine shape.

In a 38th aspect according to anyone of the preceding aspects, the one or more deflection sections include a number of deflection sections, the number of deflection sections being uneven, optionally the number of deflection sections being equal to 1, 3, 5, 7, 9 or 13; particularly the number of deflection sections being 1 or 3.

In a 39th aspect according to the preceding aspect, an uneven number of deflection sections of the one or more deflection sections is arranged opposite to an even number of deflection sections of the one or more deflection sections.

In a 40th aspect according to anyone of the preceding aspects, the one or more deflection sections include at least three deflection sections.

In a 41st aspect according to the preceding aspect, at least one of the at least three deflection sections is arranged opposite to at least two of the at least three deflection sections.

In a 42nd aspect according to anyone of the preceding aspects, the container further comprises a proximal end and a distal end opposite the proximal end.

In a 43rd aspect according to the preceding aspect, both the inlet port and the outlet port are arranged at the proximal end.

In a 44th aspect according to anyone of the two preceding aspects, the container is configured to be inserted, for use, with the distal end first into a receptacle of an apparatus for warming or cooling fluids.

In a 45th aspect according to anyone of the preceding aspects, the inlet port is configured for connecting to a fluid inlet line of a blood treatment apparatus.

In a 46th aspect according to the preceding aspect, the inlet port is configured for receiving medical fluid from the fluid inlet line through the inlet port.

In a 47th aspect according to anyone of the preceding aspects, the outlet port is configured for connecting to a fluid outlet line of a blood treatment apparatus.

In a 48th aspect according to the preceding aspect, the outlet port is configured for releasing medical fluid from the outlet port into the fluid outlet line.

In a 49th aspect according to anyone of the preceding aspects, the container is made from a substantially flexible material, optionally the material including one or more of polyurethane (PUR) and polyvinylchloride (PVC).

In a 50th aspect according to anyone of the preceding aspects, the container comprises a bag, the bag optionally comprising at least a first and a second film, the first and the second films being sealed to one another.

In a 51st aspect according to anyone of the preceding aspects, particularly during use when liquid is going through the conduit, the conduit exhibits a ratio between the maximum width and a maximum inner height (w/h) greater than 5, in particular greater than 10.

In a 52nd aspect according to anyone of the preceding aspects, during use, the fluid flow inside the conduit is a laminar flow.

In a 53rd independent aspect, there is provided an apparatus for warming or cooling medical fluids, comprising a receptacle; a heating region; a container for warming or cooling medical fluids according to any one of aspects 1 to 52 received in the receptacle; and the heating region is configured to contact at least a portion of the container for transferring heating energy to a fluid flowing through the container.

In a 54th aspect according to the preceding aspect, the heating region further comprises a first heating surface and optionally a second heating surface, the first and optional second heating surfaces being configured to contact first and second surfaces of the container for transferring heating energy to a fluid flowing through the container via the first surface and optionally the second surface.

In a 55th aspect according to anyone of the two preceding aspects, the receptacle further comprises an extension configured to receive a matching portion of the bag in order to ensure one or more of: a correct placement of the container in the receptacle, a correct orientation of the container when placed in the receptacle, a correct positioning of the container with respect the apparatus for warming or cooling fluids.

In a 56th aspect according to anyone of the three preceding aspects, the receptacle further comprises, alternatively or in combination a reference protrusion configured to engage a matching reference opening of the bag; and/or a sensor, e.g. an optical sensor, configured to sense the presence of a matching portion of the bag in an extension of the receptacle; in order to ensure one or more of a correct placement of the container in the receptacle, a correct orientation of the container when placed in the receptacle, a correct positioning of the container with respect the apparatus for warming or cooling fluids.

In a 57th independent aspect there is provided an extracorporeal blood circuit comprising a blood withdrawal line connectable to an inlet of a primary chamber of a filtration unit; a blood return line connected to an outlet of the primary chamber, the blood lines being configured for connection to a cardiovascular system of a patient; optionally a dialysis effluent line connected to an outlet of a secondary chamber of the filtration unit. The extracorporeal blood circuit further comprises a container for warming or cooling fluids according to anyone of aspects 1 to 52 connected to the blood return line or to the blood withdrawal line.

In a 58th independent aspect there is provided an apparatus for extracorporeal blood treatment comprising a filtration unit having a primary chamber and a secondary chamber separated by a semi-permeable membrane; a blood withdrawal line connected to an inlet of the primary chamber; a blood return line connected to an outlet of the primary chamber, the blood lines being configured for connection to a cardiovascular system of a patient; optionally a dialysis supply line connected to an inlet of the secondary chamber; optionally a dialysis effluent line connected to an outlet of the secondary chamber; and at least one pump to move the fluids in the lines; and a control unit driving the pump. The apparatus further comprises an apparatus for warming or cooling medical fluid according to any one of aspects 53 to 56.

In a 59th independent aspect, optionally according to anyone of the previous aspects, there is provided a container 100 for fluids comprising: an inlet port 112, inlet tubing 111 having a section diameter and being connected to the inlet port 112; an outlet port 116; and a fluid conduit configured for putting the inlet port in fluid communication with the outlet port and comprising one or more deflection sections 110, wherein the fluid conduit has a non-constant maximum width Lc in a direction of fluid flow F through the fluid conduit and a height h, the section diameter of the inlet tubing being larger than the height h of the fluid conduit; at least one of the one or more deflection sections further comprises an entry section 110e and an exit section 110x, each respective exit section being arranged downstream, in the direction of fluid flow, from each respective entry section; an inlet section 113 fluidly connecting the inlet tubing 111 with the fluid conduit, wherein the inlet section 113 comprises a first plane and a second plane, opposite to the first plane, developing from the inlet tubing 111 towards the fluid conduit and converging towards the fluid conduit.

In a 60$^{th}$ aspect according to the preceding aspect, the first plane and/or the second plane of the inlet section defines an angle with respect to a longitudinal extension of a fluid conduit main plane less than 20°, particularly included between 2° and 17°.

In a 61$^{st}$ aspect according to the preceding two aspects, the inlet section further includes a terminal portion connecting the first and second plane with the fluid conduit, the terminal portion including two respective layers substantially parallel at a distance substantially corresponding to the height h of the fluid conduit, the first plane and the second plane being connected to a respective layer of the terminal portion.

Further characteristics and advantages of the present invention will better emerge from the detailed description that follows of at least an embodiment of the invention, illustrated by way of non-limiting example in the accompanying figures of the drawings.

BRIEF DESCRIPTION OF THE DRAWINGS

The description will now follow, with reference to the appended figures, provided by way of non-limiting example, in which:

FIGS. 7A to 7D show fluid flow based on different alternative embodiments of inlet sections in accordance with embodiments of the present invention;

DETAILED DESCRIPTION

Figure 1:
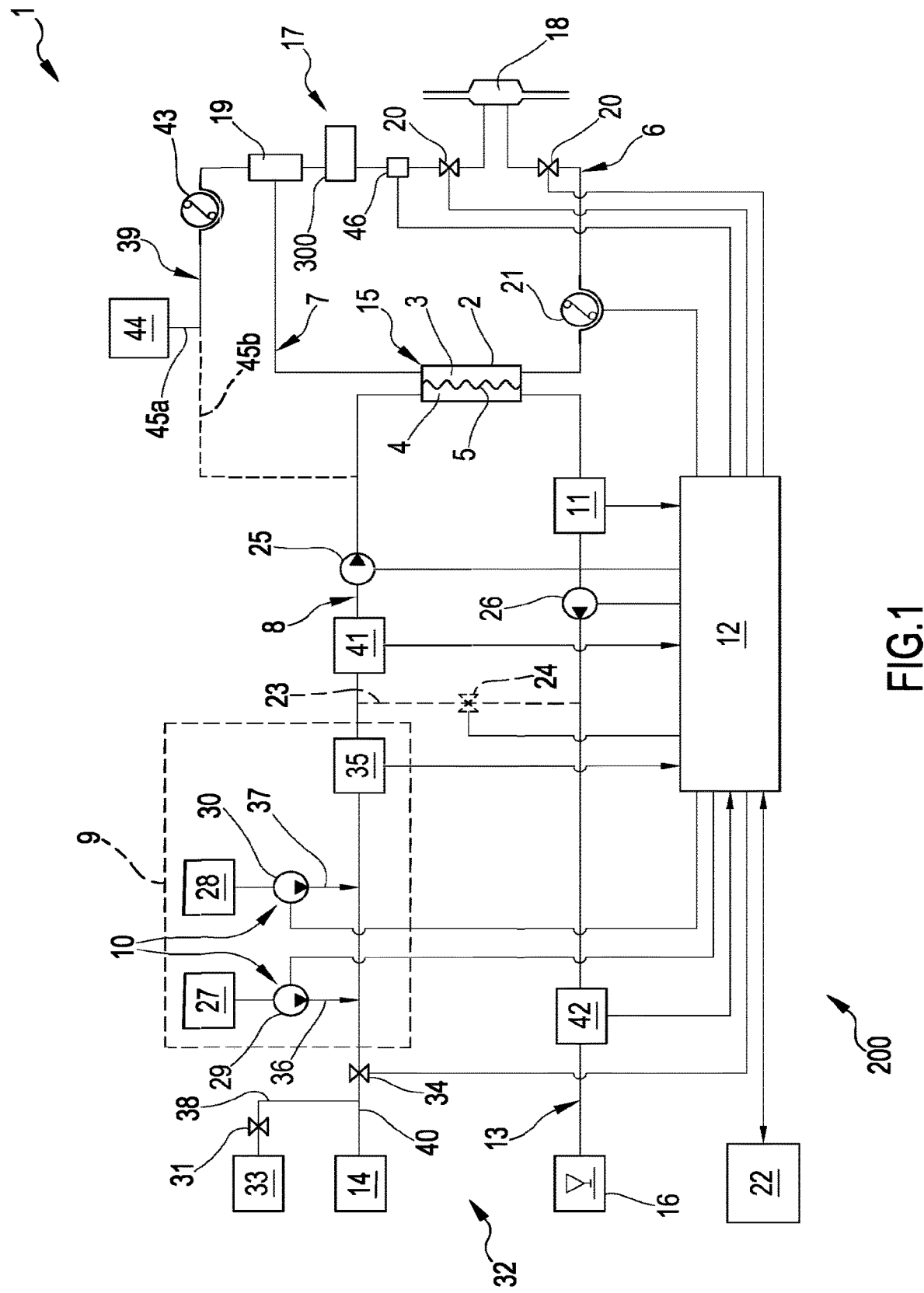
FIG. 1 schematically represents an extracorporeal blood treatment apparatus in accordance with an illustrating embodiment.

FIG. 1 schematically represents an extracorporeal blood treatment apparatus 1 in accordance with an illustrating embodiment.

An example of an extracorporeal blood treatment circuit 200 is schematically illustrated, but it is noted that the specific structure of the extracorporeal blood treatment circuit 200 is not relevant for the purposes of the present invention and therefore other and different circuits to those specifically shown in FIG. 1 might be used in consequence of the functional and design needs of each single medical apparatus (e.g. continuous renal replacement treatments—CRRT treatments—vs chronic dialysis treatments).

The extracorporeal blood treatment circuit 200 exhibits a dialysis fluid circuit 32 having a dialysis fluid supply line 8, configured to transport a dialysis liquid from at least one source 14 towards a treatment station 15 where one or more filtration units 2, or dialyzers, operate.

The dialysis fluid circuit 32 further comprises a dialysis effluent line 13, configured for the transport of a dialysate liquid (spent dialysate and liquid ultrafiltered from the blood through a semipermeable membrane 5) from the treatment station 15 towards an evacuation zone, schematically denoted by 16 in FIG. 1.

The hydraulic circuit cooperates with a blood circuit 17, also schematically represented in FIG. 1 in its basic component parts. The specific structure of the blood circuit is also not fundamental to the present invention. Thus, with reference to FIG. 1, a brief description of a possible embodiment of a blood circuit is made, which is however provided purely by way of non-limiting example.

The blood circuit 17 of FIG. 1 comprises a blood withdrawal line 6 configured to remove blood from a vascular access 18 and a blood return line 7 configured to return the treated blood to the vascular access 18.

The blood circuit 17 of FIG. 1 further comprises a primary chamber 3, or blood chamber, of the blood filtration unit 2, the secondary chamber 4 of which is connected to the extracorporeal blood treatment circuit 200.

In greater detail, the blood withdrawal line 6 is connected to the inlet of the primary chamber 3, while the blood return line 7 is connected to the outlet of the primary chamber 3.

In turn, the dialysis supply line 8 is connected to the inlet of the secondary chamber 4, while the dialysis effluent line 13 is connected to the outlet of the secondary chamber 4.

The filtration unit 2, for example a dialyzer, a plasma filter, a hemofilter, or a hemodiafilter, comprises, as mentioned, the two chambers 3 and 4, which are separated by a semipermeable membrane 5, for example of the hollow-fiber type or of the plate type.

In an embodiment, the filtration unit (2) may include an adsorption device, such as a plasma filtration adsorption device, a charcoal column, an adsorption device for endotoxin removal for e.g. sepsis treatment; in this embodiment, both a fresh dialysis fluid line and a dialysis effluent line to remove spent dialysis fluid may not be present.

The blood circuit 17 may also comprise one or more air separators 19 and clamps 20 on both withdrawal and return line.

The extracorporeal blood treatment apparatus 1 comprises one or more blood pumps 21, for example positive displacement pumps such as peristaltic pumps; in the example of FIG. 1, a blood pump 21 is included on the blood withdrawal line 6.

The apparatus of the above-described embodiment may also comprise a user interface 22 (e.g. a graphic user interface or GUI) and a control unit 12, i.e. a programmed/programmable control unit, connected to the user interface.

A bypass line 23 connects the dialysis fluid supply line 8 and the dialysis effluent line 13, thereby bypassing the filtration unit 2, and one or more fluid check members 24 connected to the control unit 12 selectively opens and closes the bypass line 23.

A dialysis fluid pump 25 and a dialysate pump 26 may be included, located respectively on the dialysis fluid supply line 8 and on the dialysis effluent line 13 and further operatively connected to the control unit 12.

The apparatus may also comprise a dialysis fluid source such as one or more bags of fresh fluid (e.g. in CRRT treatment) or a dialysis fluid preparation device 9 (e.g. in chronic treatment), which may be of any known type, for example including one or more concentrate sources 27, 28 and respective concentrate pumps 29, 30 (regulating means 10) for the delivery, as well as at least a conductivity sensor 35.

Due to the dialysis apparatus potentially comprising various liquid sources (e.g. one or more water sources 14, one or more concentrate sources 27, 28, one or more sources 33 of disinfectant liquids) connected to the dialysis supply line 8 with respective delivery lines 36, 37, 38 and 40, the apparatus may exhibit, at each delivery line, a respective check member (not all are shown in FIG. 1) and, for example, comprising a valve member 31 and 34.

Arranged in the dialysis supply line 8, in the direction in which the liquid circulates, there are the first flow meter 41 and the dialysis fluid pump 25.

The dialysis effluent line 13 may be provided with a dialysate pump 26 and a second flow meter 42. The first and second flow meters 41, 42 may be used to control (in a known manner) the fluid balance of a patient connected to the blood circuit 17 during a dialysis session.

A sensor 11 is provided on the dialysis effluent line 13, immediately downstream the filtration unit 2, to measure a parameter value (e.g. conductivity) of the dialysate in the dialysis effluent line 13.

One or more infusion lines 39 may also be included, with respective infusion pumps 43 or flow regulation valves, the infusion lines being connected up to the blood return line 7 and/or the blood withdrawal line 6 and/or directly to the patient. The liquid sources for the infusion lines may be pre-packaged bags 44 and/or liquids prepared by the apparatus itself. The infusion line 39 may either receive infusion liquid from a pre-packaged bag 44 (solid line 45*a*) or from an online preparation through-branch 45*b* (dotted line).

As already mentioned, the described embodiments are intended to be non-limiting examples.

Figure 4:
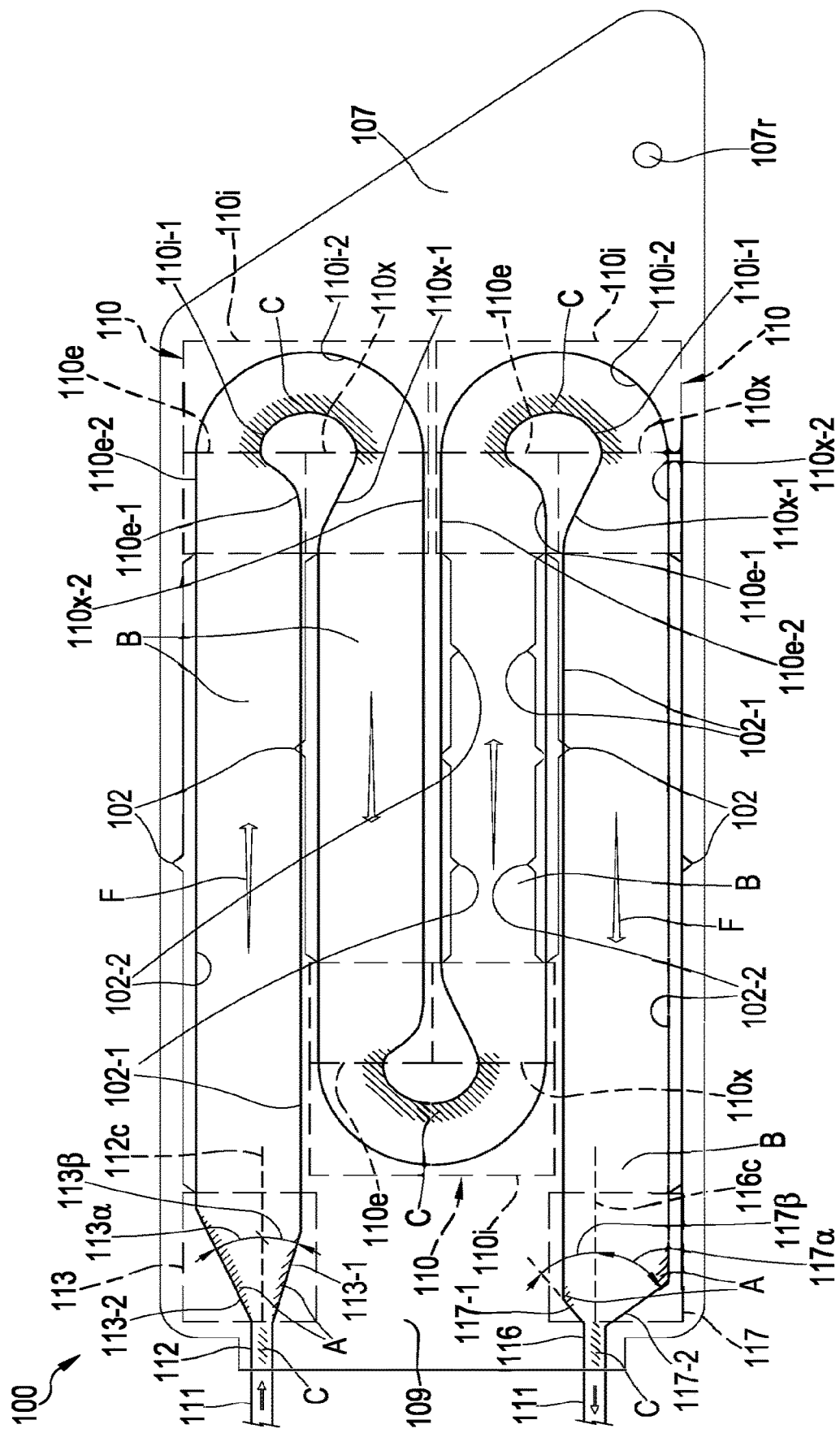
FIG. 4 shows a bag for an apparatus for warming fluids, the bag being in accordance with a first embodiment of the present invention.

In FIG. 1, the blood return line 7 may be provided with a bag 100 for circulating fluids therein (a bag embodiment is represented in FIG. 4) before returning blood to the patient.

The extracorporeal blood treatment machine is provided with an apparatus 300 for e.g. warming fluids circulating in the bag in order to regulate a temperature of the blood returned to the patient to a desired temperature region, for example around 37° C.

In the following description, reference is made to a fluid warming apparatus to regulate blood temperature and to a corresponding warming bag. However, the description should not be interpreted in a limitative way in this respect. An apparatus for temperature fluid control is included in the scope of the appended claims. A bag for either warming or cooling is also encompassed by the present description and claims.

Fluid warming apparatus 300 is generally designed to regulate the temperature of (e.g. to warm) medical fluids such as blood or infusion/substitution liquid. Fluid warming apparatus 300 may be employed to warm medical fluids other than blood intended to be returned or fluids intended to be supplied to the body of a patient, for example when regulating the temperature of treatment solution entering filtration unit 2. In other terms, the bag 100 may be differently connected to the dialysis line 8. Thus, fluid warming apparatus 300 may be employed in a manner other than that illustrated in FIG. 1. In the illustrative embodiment shown in FIG. 1, fluid warming apparatus 300 is employed to warm the blood being returned to the patient and coming from air separator 19. An air detector 46 and a clamp 20 may be arranged on blood line 7 downstream from the fluid warming apparatus 300 and upstream from vascular access 18.

Given the above description of a possible embodiment of extracorporeal blood treatment apparatus, thereafter specific embodiments of the apparatus 300 for e.g. warming fluids and of a bag 100 for fluids are described.

Figure 2:
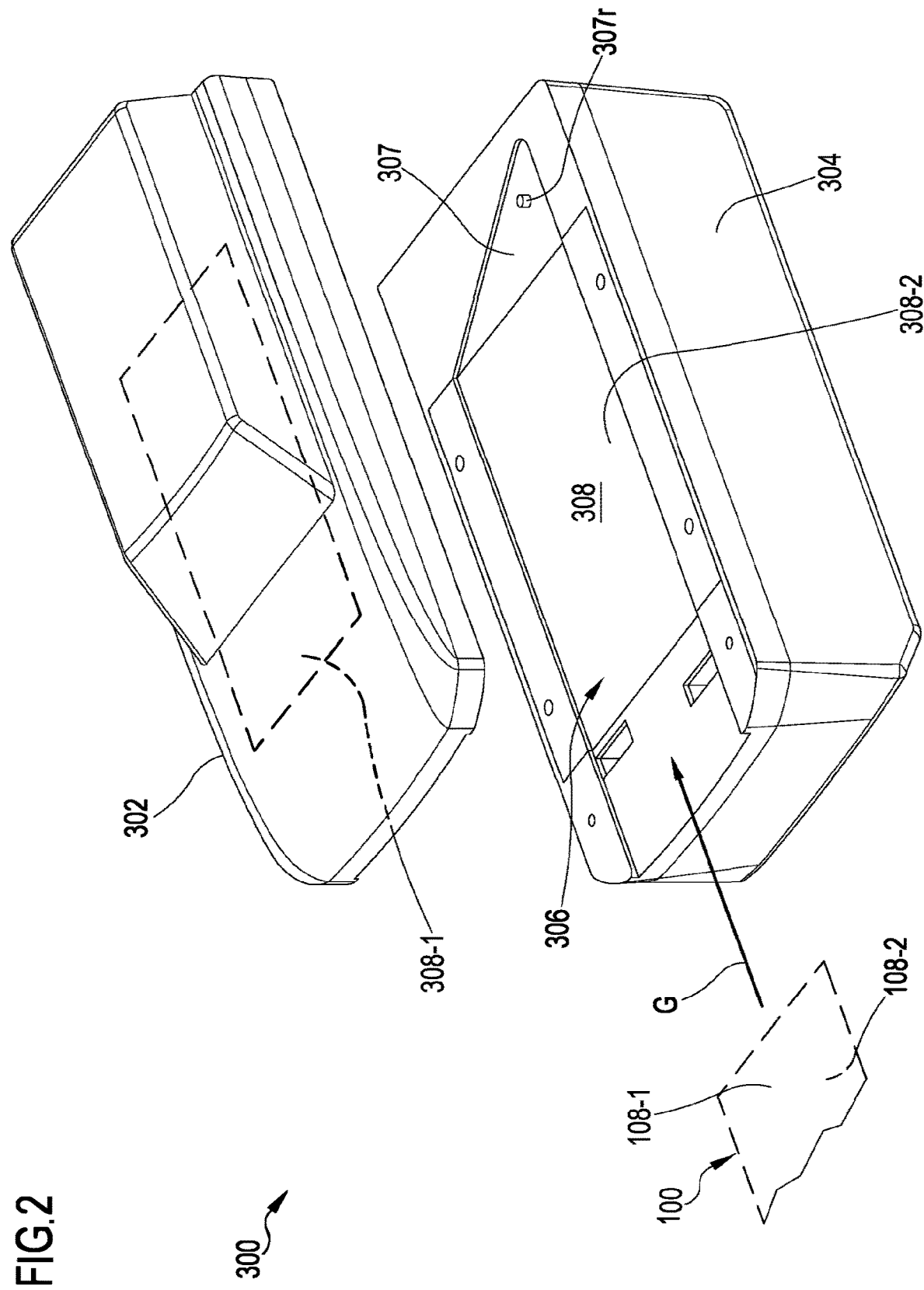
FIG. 2 shows, schematically and in partially exploded view, an apparatus for warming fluids in accordance with embodiments of the present invention.

FIG. 2 shows, schematically and in partially exploded view, an apparatus 300 for warming fluids in accordance with embodiments of the present invention. Fluid warming apparatus 300 may generally be designed as shown, namely configured to e.g. substantially horizontally receive, in a slot 306, a bag 100 for e.g. warming fluids between a first 302 and a second 304 component, defining a heating region 308 between the first 302 and second 304 components. The apparatus 300 may be designed with first 302 and second 304 components pivotably connected to one another, thereby facilitating cleaning of heating region 308. First 302 and second 304 components may, however, also be connected to one another in any other suitable manner (e.g. disconnection, shifting, tilting), thereby facilitating cleaning and/or insertion/removal of bag 100. In the embodiment shown, first 302 and second 304 components are shown separated from one another for clarity. During use, first 302 and second 304 components are fixedly mounted to one another, thereby providing slot 306 for insertion/removal of bag 100. As shown, a bag 100 may be inserted into slot 306 and, thus, positioned in superimposition with the heating region 308. Slot 306 may be provided with an extension 307 in order to receive a matching portion 107 of bag 100. Portion 107 may be in the form of a small tab protruding from one side of the bag 100 (see FIG. 8*a*) or triangular shaped as shown in FIGS. 2 and 4. Further, extension 307 of slot 306 may be provided with a reference protrusion 307*r* configured to engage a corresponding reference opening 107*r* in bag 100. Tab, extension 307 and/or reference protrusion 307*r* are designed to ensure proper placement of bag 100 into slot 306 as described with respect to bag 100 further below.

The heating region 308 typically comprises heating surfaces between which, during use, a bag 100 is positioned, having a large portion of its outer surfaces in contact with the heating surfaces. As shown in FIG. 2, a bag 100 would present substantially flat upper 108-1 and lower 108-2 surfaces that may be brought into superimposition with corresponding upper 308-1 and lower 308-2 (e.g. upper and lower) heating surfaces of heating region 308.

Figure 3:
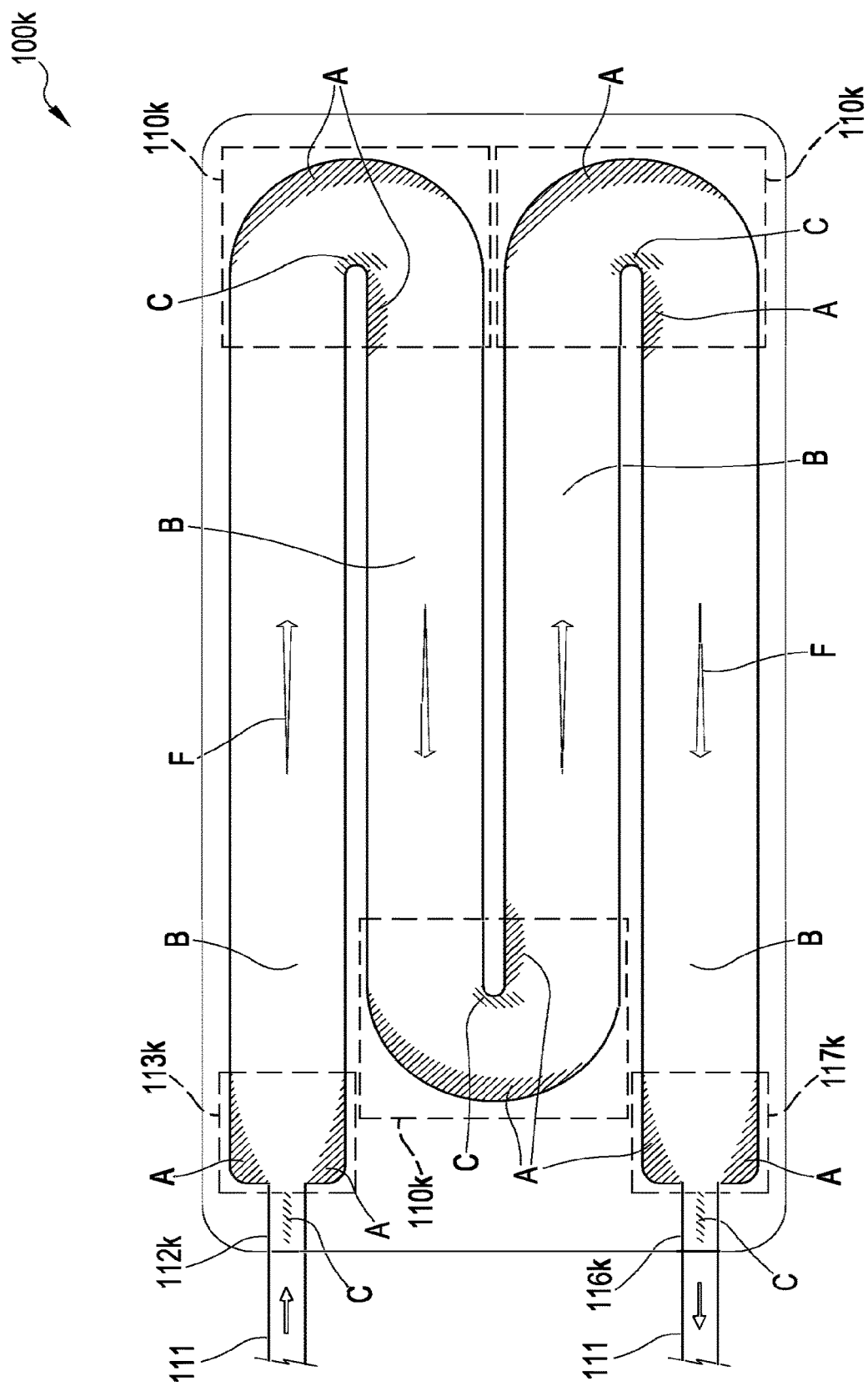
FIG. 3 shows a bag for warming fluids in accordance with a prior art design.

FIG. 3 shows a bag 100*k* for warming fluids in accordance with a prior art design. The bag 100*k* may generally be used with an apparatus similar or identical to apparatus 300 for warming fluids as shown in FIG. 2 and as described above.

According to the prior art design, bag 100*k* is made from two adjacent layers of film material, for example plastic film, that are welded to one another in a specific manner in order to form a conduit for fluid to be heated. The conduit puts an inlet port 112*k* into fluid communication with an outlet port 116*k*. The conduit further includes an inlet section 113*k* adjacent to inlet port 112*k* and an outlet section 117*k* adjacent to outlet port 116*k*. As shown in FIG. 3, the conduit further includes three deflection sections 110*k*, connecting the elongated sections of bag 100*k* with one another and, respectively, with the inlet section 113*k* and the outlet section 117*k*, providing the conduit with a generally meandering shape.

As shown in FIG. 3, inlet section 113*k*, deflection sections 110*k*, outlet section 117*k*, and elongated sections in between typically have substantially the same cross-section, with little or no variation in the width and/or cross-section of the conduit over any of the sections.

The direction of fluid flow F is shown in FIG. 3 for each of the elongated sections and is generally directed from the inlet port 112k towards the outlet port 116k. As illustrated, fluid flowing through the conduit from inlet port 112k towards outlet port 116k enters the conduit at the inlet section 113k and exits the conduit at outlet section 117k. The fluid is also deflected according to the meandering shape of the conduit at the deflection sections 110k. The fluid flow profile through the conduit is dependent on the geometry of the conduit in the respective sections (e.g. inlet section, outlet section, elongated section(s), deflection section(s)), flow rate and viscosity. While the fluid flow is relatively fully developed over the elongated sections, it varies with respect to a number of fluid flow parameters throughout the sections of the conduit.

As can be seen from FIG. 3, fluid flow through the conduit exhibits regions A of fluid flow having a relatively lower velocity or even stagnating, regions B of relatively homogeneous fluid flow, and regions C of fluid flow having relatively higher velocity.

Low velocity fluid flow may entail substantial disadvantages, for example areas with little or no exchange of fluid due to the formation of stagnation areas and/or to the collection or accumulation of air bubbles in areas of low fluid flow. If the fluid conveyed through the conduit is blood, low velocity fluid flow may lead to clotting, entailing the risk of blood clots being created, being carried away by the blood flow, and ultimately being returned to the patient in the blood flow. This is particularly likely in case of stagnation of fluid, when regions are formed in which little or no fluid flow occurs and where little to none exchange of fluid with the mass of fluid flowing through the conduit takes place. Low velocity fluid flow is, thus, to be avoided.

Low velocity fluid flow, denoted in FIG. 3 as regions A, may occur at the inlet section 113k, at the outlet section 117k, and at the deflection section 110k. The shape of the deflection sections 110k may significantly contribute to the formation of low velocity fluid flow, in particular in the intermediate section thereof (see region A along an outer edge of the intermediate section) and in the exit section thereof (see region A located at an inner edge of the exit section, downstream from the intermediate section).

High velocity fluid flow may also entail disadvantages, for example excessive pressure drop between the inlet and the outlet of the container and high shear stress in the near container wall vicinity.

High velocity fluid flow, denoted in FIG. 3 as regions C, may occur near the inlet section 113k, near the outlet section 117k, and at the deflection section 110k. High velocity fluid flow, occurring near the inlet section 113k or near the outlet section 117k is typically less critical, since the higher velocity is generally caused by the fluid flowing from medical tubing through the inlet port 112k (or towards the outlet port 116k), which is typically provided with a smaller cross-section than that of the conduit. However, high velocity fluid flow occurring near the inlet section 113k or near the outlet section 117k may have detrimental effects as well.

The shape of the fluid path geometry (in combination with fluid flow rate and viscosity) causes low/high velocity regions for the fluid. High velocity fluid flow occurring at the deflection section 110k typically occurs at an inner edge of the intermediate section thereof. Excessively high velocity fluid flow is to be avoided since it may cause blood haemolisis.

Figure 8A:
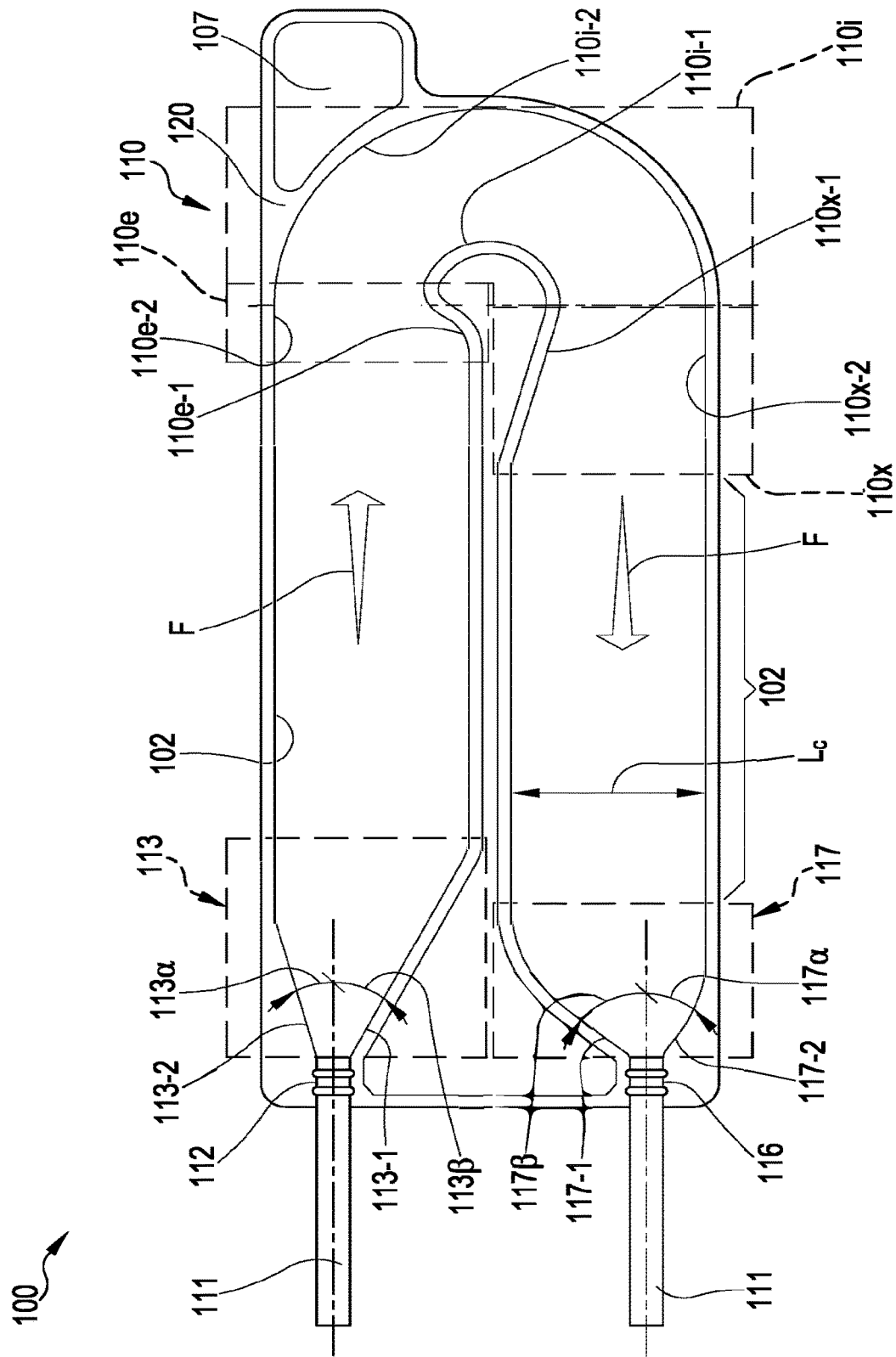
FIG. 8A shows a bag for an apparatus for warming fluids, the bag being in accordance with another embodiment of the present invention.

FIG. 4 shows a bag 100 for an apparatus 300 for warming fluids, the bag 100 being in accordance with a first embodiment of the present invention. FIG. 8A shows a second embodiment of bag 100 particularly designed for high flow rates. The bag 100 is flexible and in particular made of a film material.

The bag 100 may be made from two layers of film material, particularly polyurethane (PUR) or polyvinylchloride (PVC), superposed and welded to form the bag 100 and to form a conduit delimited by the two layers and by the lines of welding. Lines of welding are not shown in FIG. 4 for clarity. For illustration purposes, lines of welding 120 are shown in the detailed view of FIG. 5.

Polyurethane (PUR) is a material having high mechanical resistance and good thermal transfer properties. Therefore, the use of PUR may provide bag 100 with advantageous properties regarding heat transfer through the film material and to the fluid inside bag 100. The use of PUR may further minimize the risk of leakage of fluid from bag 100.

The embodiment shown in FIG. 4 is provided with four connection sections 102 arranged substantially parallel to one another in a layout exhibiting a substantially side-by-side arrangement of the four connection sections 102.

Vice versa, the embodiment shown in FIG. 8A is provided with two connection sections 102 only. It is noted that the connection sections 102 are shown as parallel to an overall development direction of bag 100 (e.g. substantially parallel to directions F and/or the direction of fluid inflow and outflow—see arrows near element 111). However, connection sections 102 may be arranged at an angle (e.g. orthogonal) with respect to the overall development direction and/or with respect to one another. In the latter case, the cross-section and/or maximum width $L_c$ of the conduit may increase or decrease to a certain extent along the length of any of the sections (e.g. connection sections, deflection sections, etc.).

The terms width and cross-section both pertain to a measure of cross sectional size of the conduit and its sections and are used to reflect the different states of bags 100 before and during use. As the bags 100 are made of layers of plastic film, a bag has, before use, a substantially flat shape, due to the conduit not containing any liquid or particles. In this unused state, the size of the conduit may be referred to as having a width, since the width of the flat conduit is an effective measure thereof. During use, however, the fluid being conveyed through the conduit causes the two layers of film to cease contacting each other, thereby opening up the conduit vertically and facilitating fluid flow. In this used state, the size of the conduit may be referred to as having a cross-section, since the cross-section (or cross section area) is an effective measure thereof. Typically, in one embodiment (FIG. 4) the cross section of the conduit has, during use, a size of approximately 1-2 mm (height)×18-22 mm (width), in particular about 1.4 mm×20 mm. The width or maximum width $L_c$ of the conduit, when the bag is not used (i.e. flat), is approximately 20 mm. In some embodiments (FIG. 8A), the cross section of the conduit may be larger; the cross section of the conduit has, during use, a size of approximately 1-2 mm (height)×34-45 mm (width), in particular about for example 1.4 mm×40 mm, for high flow applications. It is noted that the main principles of the overall design, in particular those of having a conduit with a width that is much larger than its height (i.e. substantially 2D flow with width >>height) and the conduit being designed for laminar flow, may be applied in a broad range of applications and is not restricted to the dimensions given (e.g. with respect to the application for blood warmer bags).

In this respect several properties may be adjusted for individual applications, for example the relation between the heat exchange surface area with respect to a target performance (e.g. W×L, conduit width×conduit length), minimum/maximum shear rates in the target flow operating range (e.g. depending on width and height of the conduit), and pressure drop (e.g. depending on width, height, and length of the conduit).

In this respect when referring to 2D flow, it is intended that the fluid flows in a channel having a width much higher than the height so that, though being of course the flow three dimensional, it may be considered substantially bi-dimensional. In more detail, the ratio between the width and the height is higher than 5 ($L_c/h>5$), possibly higher than 10. The two examples of FIGS. 4 and 8A have a ratio $L_c/h$ of more than 10.

Moreover, the present bag embodiments are more advantageous in presence of, though not limited, and particularly designed for laminar flow conditions inside the bag.

Generally referring to the disclosed embodiments (FIGS. 4 and 8A), opposite ends of the meandering conduit are arranged on the same side of bag 100 and are provided with an inlet section 113 and an outlet section 117. The inlet section 113 and the outlet section 117 are further connected to an inlet port 112 and an outlet port 116, respectively. The inlet 112 and outlet 116 ports may further include a tube or medical fluid line 111 and/or a Luer connector (not shown). The Luer connectors may be arranged at an opposite end of the tubes 111. In particular tube 111 connected to the inlet 112 may be provided with a male Luer connector and tube 111 connected to the outlet 116 may be provided with a female Luer connector so to avoid erroneous connection of the bag 100 to the extracorporeal blood circuit. In some embodiments, the Luer connectors may be arranged adjacent to inlet port 112 and/or outlet port 116, respectively. The tubes may also be made from, for example, PVC or PUR.

More generally, the inlet 112 is provided with a connector configured to be coupled with a respective counter connector on the return line 7 placed downstream the filtration unit 2 and possibly downstream the air separator 19, but immediately upstream the warmer unit 300 and upstream the air detector 46; the outlet 116 is provided with a connector configured to be coupled with a respective counter connector on the return line 7 placed immediately downstream the warmer unit 300 and upstream the air detector 46; the inlet and outlet connectors and the counter connectors are configured to be coupled only in the correct configuration (i.e. the inlet connector may not be coupled to the outlet counter-connector and the outlet connector may not be coupled to the inlet counter-connector).

Adjacent connection sections 102 are joined together and put in fluid communication by means of deflection sections 110. Deflection sections 110 define rounded bends that provide the conduit with an overall meandering (or serpentine) shape. Each deflection section 110 includes a respective entry section 110e, a respective intermediate section 110i, and a respective exit section 110x, arranged in sequence based on fluid flow through the conduit (see arrows F in FIGS. 4 and 8A).

As shown in FIG. 4 and FIG. 8A, the entry section 110e, the intermediate section 110i, and the exit section 110x of each deflection section 110 are provided with a specific shape in order to avoid one or more of the problems mentioned above associated with prior art designs. In the embodiments shown, the entry section 110e provides the conduit with a decrease in the maximum width (or internal diameter) from the adjacent connection section 102 (having a larger width/diameter) towards the adjacent intermediate section (having a smaller width/diameter). The exit section 110x provides the conduit with an increase in the maximum width (or internal diameter) from the adjacent intermediate section (having a smaller width/diameter) towards the adjacent connection section 102 (having a larger width/diameter). Intermediate section 110i is shown as having a substantially constant width/diameter.

The individual shapes of entry section 110e and exit section 110x are different from one another. Entry section 110e includes an inner edge 110e-1 and an outer edge 110e-2, inner and outer being defined with respect to the corresponding intermediate section 110i, which defines an outer edge 110i-2 (i.e. the outside of the bend) and an inner edge 110i-1 (i.e. the inside of the bend). The inner edge 110e-1 of entry section 110e is provided with a nonlinear shape (e.g. corresponding substantially to a segment of a circle) while the outer edge 110e-2 of entry section 110e is provided with a straight shape (e.g. continuing straight and in extension from the corresponding outer edge 102-2 of the preceding connection section 102). The nonlinear shape of the inner edge 110e-1 of entry section 110e determines the decrease in width/cross-section of the conduit from the preceding connection section 102 to the following intermediate section 110i.

With respect to the terms "inner edge" and "outer edge" in connection with connection sections 102, the following is noted. For connection sections 102, which are provided to connect deflection sections 110 with one another, the terms "inner" and "outer" with respect to the edges of a connection section 102 pertain to the respective nearest deflection section 110. FIG. 4 shows this naming convention for reasons of clarity only for one of the two connection sections 102 provided for connection deflection sections 110 with one another (see the second and third connection section 102 in direction of fluid flow F). In direction of fluid flow F, the third connection section 102 is provided with reference numerals showing the respective inner and outer edges thereof. Thus, the top edge (i.e. the edge closer to the top of FIG. 4) of the third connection section 102 is marked as inner edge 102-1 near the second deflection section 110 (in direction of fluid flow F, and adjacent to identification region 109). The bottom edge (i.e. the edge closer to the bottom of FIG. 4) of the third connection section 102 is marked, along the same section of the conduit, as outer edge 102-2 near the second deflection section 110.

Correspondingly, the top edge of the third connection section 102 is marked as outer edge 102-2 near the third deflection section 110 (in direction of fluid flow F, and adjacent to portion 107). The bottom edge of the third connection section 102 is marked, along the same section of the conduit, as inner edge 102-1 near the third deflection section 110. In this manner, the terms "inner" and "outer" always correspond to the nearest deflection section 110. Therefore, the terms "inner" and "outer" change in direction of fluid flow F along the conduit depending on the nearest deflection section 102, thereby clearly identifying the portions of connection sections 102 which are referred to as inner 102-1 and outer 102-2 edges.

It is noted that the above also applies to the remaining connection sections 102, which are provided to connect deflection sections 110 to one another (i.e. it applies also to the second connection section 102 shown in FIG. 4). Not all reference numerals have been added to FIG. 4, however, for reasons of clarity. It is further noted that the above also applies in embodiments having fewer or more connection sections 102 than the embodiment shown in FIG. 4 (e.g. having 2 or 6 or more connection sections 102).

In both embodiments of FIGS. 4 and 8A, similar to entry section 110e, exit section 110x includes an inner edge 110x-1 and an outer edge 110x-2, inner and outer being defined with respect to the corresponding intermediate section 110i in the same manner as described with respect to entry section 110e above. The inner edge 110x-1 of exit section 110x is provided with a substantially linear shape (e.g. substantially corresponding to a line segment positioned at an angle with respect to the corresponding edge of the following connection section 102) while the outer edge 110x-2 of exit section 110x is provided with a straight shape (e.g. leading straight and in extension to the corresponding edge of the following connection section 102). The angular configuration of the inner edge 110x-1 of exit section 110x with respect to the corresponding edge of the adjacent (following) connection section 102 determines the increase in width/cross-section of the conduit from the intermediate section 110i to the following connection section 102.

In the embodiment shown in FIG. 4, the conduit of bag 100 includes three deflection sections 110. All deflection sections 110 are substantially identical to one another, apart from having a mirror-inverted layout depending on the deflection section 110 determining a right turn or a left turn (in direction of fluid flow and as seen from the top; see FIG. 4). Thus, the description of entry sections 110e, intermediate sections 110i, and exit sections 110x is applicable to any one of the deflection sections 110 shown in FIG. 4. It is noted that, depending upon the deflection section 110 determining a right turn or a left turn, the positions of "inner" and "outer" edges changes accordingly, so that with respect to the connection sections 102 the terms "inner" and "outer" receive their respective meaning in relation to the deflection section 110, which is referred to in the respective context (i.e. based on a respective inlet end or outlet end of a connection section 102).

As can be seen from FIG. 4 (and similarly for embodiment of FIG. 8A), the fluid flow through the conduit defined by bag 100 is rather homogeneous. At the intermediate sections 110i of the deflection sections 110, there is little to no stagnation or regions of low velocity fluid flow. This is achieved by a moderate overall increase in fluid flow velocity in the intermediate sections 110 due to the decrease in width/cross-section in the respective entry section 110e, which is maintained throughout the intermediate section 110i. Further, the region of high velocity fluid flow (see region C—FIG. 4) is less focused/localized and spreads across a longer and wider portion of the deflection section 110. This reduces or minimizes shear stress and causes the high velocity fluid flow in region C to be more homogeneous.

Another effect of the individual configuration of the deflection sections 110 is that there is little to no low velocity fluid flow (and no stagnation) in the respective exit sections 110x of the deflection sections 110. This is achieved both by the particular configuration of the exit section 110x and by the less focused/localized and more spread-out region C of high velocity fluid flow throughout the intermediate sections 110i.

The ratio between the width/cross-section of the connection sections 102 and the width/cross-section of intermediate sections 110 ranges between 0.5 and 0.85, particularly between 0.7 and 0.8.

Tests have been conducted with different fluid flow rates. At lower flow rates of, for example, 100 ml/min, the effect of the individual configuration of the deflection sections 110 in line with the embodiment shown in FIG. 4 is more pronounced. However, the effect may also be significant as compared to known designs at higher fluid flow rates of, for example, 200 ml/min or 300 ml/min, at which the beneficial effects described above also continue to occur.

The bag 100 in accordance with the present invention may further include inlet 113 and outlet 117 sections configured to improve fluid flow through the conduit. In some embodiment either one or both of inlet port 112 and outlet port 116 may be arranged excentrically with respect to a main development axis of the adjacent connection section 102.

In the embodiment shown in FIGS. 4 and 8A, inlet port 112 and outlet port 116 are arranged excentrically with respect to the respective connection section 102 respectively putting the inlet 113 and outlet 117 sections in fluid communication with the following/preceding deflection section 110. In the embodiment of FIG. 4, inlet port 112 is arranged substantially parallel to the adjacent connection section 102 and slightly (laterally) shifted towards the center of bag 100 (e.g. towards and parallel to outlet port 116). In the embodiment of FIG. 8A, inlet port 112 is arranged substantially parallel to the adjacent connection section 102 and slightly (laterally) shifted away from the center of bag 100 (e.g. away from and parallel to outlet port 116).

In accordance with this placement of the inlet port 112, inlet section 113 is provided with an asymmetrical configuration, presenting an inner edge 113-1 and an outer edge 113-2, both positioned at an angle with respect to an axis 112c of inlet port 112. Angles 113β and 113α of the inner 113-1 and outer 113-2 edges may be different from one another or the same. In some embodiments, due to the inlet port 112 not being centered with respect to the adjacent connection section 102, the inner 113-1 and outer 113-2 edges of inlet section 113 may have different lengths, even if angles 113β and 113α are the same. Inlet section 113 provides the conduit with a diverging region, increasing the width/cross-section of the conduit from the diameter of the inlet port 112 to the cross-section of the adjacent connection section 102.

The outlet section 117 is provided with inner 117-1 and outer 117-2 edges in a similar manner as described with respect to inlet section 113 above. In the embodiment of FIG. 4, outlet port 116 is arranged substantially parallel to the adjacent connection section 102 and slightly (laterally) shifted towards the center of bag 100 (e.g. towards and parallel to inlet port 112). In the embodiment of FIG. 8A, outlet port 116 is arranged substantially parallel to the adjacent connection section 102 and slightly (laterally) shifted away from the center of bag 100 (e.g. away from and parallel to inlet port 112)

In accordance with this placement of the outlet port 112, outlet section 117 is provided with an asymmetrical configuration, presenting an inner edge 117-1 and an outer edge 117-2, both positioned at an angle with respect to a central axis 116c of port 116. The angles 117β and 117α of the inner 117-1 and outer 117-2 edges may be different from one another or the same. Due to the outlet port 116 not being centered with respect to the adjacent connection section 102, inner 117-1 and outer 117-2 edges may have different lengths, even if angles 117α and 117β are the same. Outlet section 117 provides the conduit with a converging region, decreasing the width/cross-section of the conduit from the cross-section of the adjacent connection section 102 to the diameter of the outlet port 116.

Additionally, the inlet 113 and outlet 117 sections are provided with different shapes due to the direction of fluid flow being different for the two sections. In other words, the diverging region of inlet section 113 has a shape different from the converging region of the outlet section 117 (see FIGS. 4 and 8C).

In both embodiments, the inlet section 113 is provided with inner 113-1 and outer 113-2 edges that form a smaller angle with respect to the corresponding edge of the adjacent connection section 102 than corresponding angles formed by inner 117-1 and outer 117-2 edges of outlet section 117. It was found that regions A exhibiting lower velocity fluid flow at the inlet section 113 (see corresponding inlet section 113k in FIG. 3 for comparison) may be substantially reduced by providing the inlet section 113 with a gradually increasing (w.r.t. direction of fluid flow) width/cross-section that increases the width/cross-section over a longer distance of fluid flow through the conduit.

Likewise, regions A exhibiting lower velocity fluid flow at the outlet section 117 (see corresponding outlet section 117k in FIG. 3 for comparison) may be substantially reduced by providing the outlet section 117 with a gradually decreasing (w.r.t. direction of fluid flow) width/cross-section that decreases the width/cross-section over a shorter distance of fluid flow through the conduit. The reduction of regions A exhibiting lower velocity fluid flow at both the inlet 113 and outlet 117 sections was most pronounced in combination with the asymmetrical arrangement of inlet 112 and outlet port 116 as shown in FIGS. 4 and 8C.

In some embodiments, two layers of plastic film (e.g. PUR or PVC) form a portion 107, located on the side of bag 100 opposite to the inlet/outlet ports and adjacent to the conduit. The portion 107 may be in the form of a tab (FIG. 8A) emerging from a lateral area on the side opposite to inlet/outlet; alternatively the portion may be optionally triangular as shown in the annexed FIG. 4 by way of non-limiting example. The portion 107 is designed to fit into a correspondingly counter-shaped portion of slot 306 of the fluid warming apparatus 300. In some embodiments, the portion 107 is provided with a reference opening 107r. Reference opening 107r is designed to fit with a corresponding protrusion provided in slot 306 of the fluid warming apparatus 300. Triangular portion 107 and/or reference opening 107r are positioned with respect to remaining components of bag 100 in order to ensure proper placement of bag 100 into slot 306 of the fluid warming apparatus 300. In some embodiments, bag 100 is inserted into apparatus 300 generally along insertion direction G.

Alternatively (or in combination) a sensor, e.g. an optical sensor) may be used to sense the presence of the bag 100, i.e. to sense the presence of the (tab/triangular) portion 107.

Proper placement includes, for example, inlet/outlet tubes engaged in corresponding recesses and the conduit being placed in superimposition with heating region 308.

Bag 100 may further include, particularly in an identification region 109 between inlet 112 and outlet 116 ports, which is not occupied by portions of the conduit, an area configured for placing a machine- or human-readable label, indicating, for example, properties of bag 100.

Figure 5:
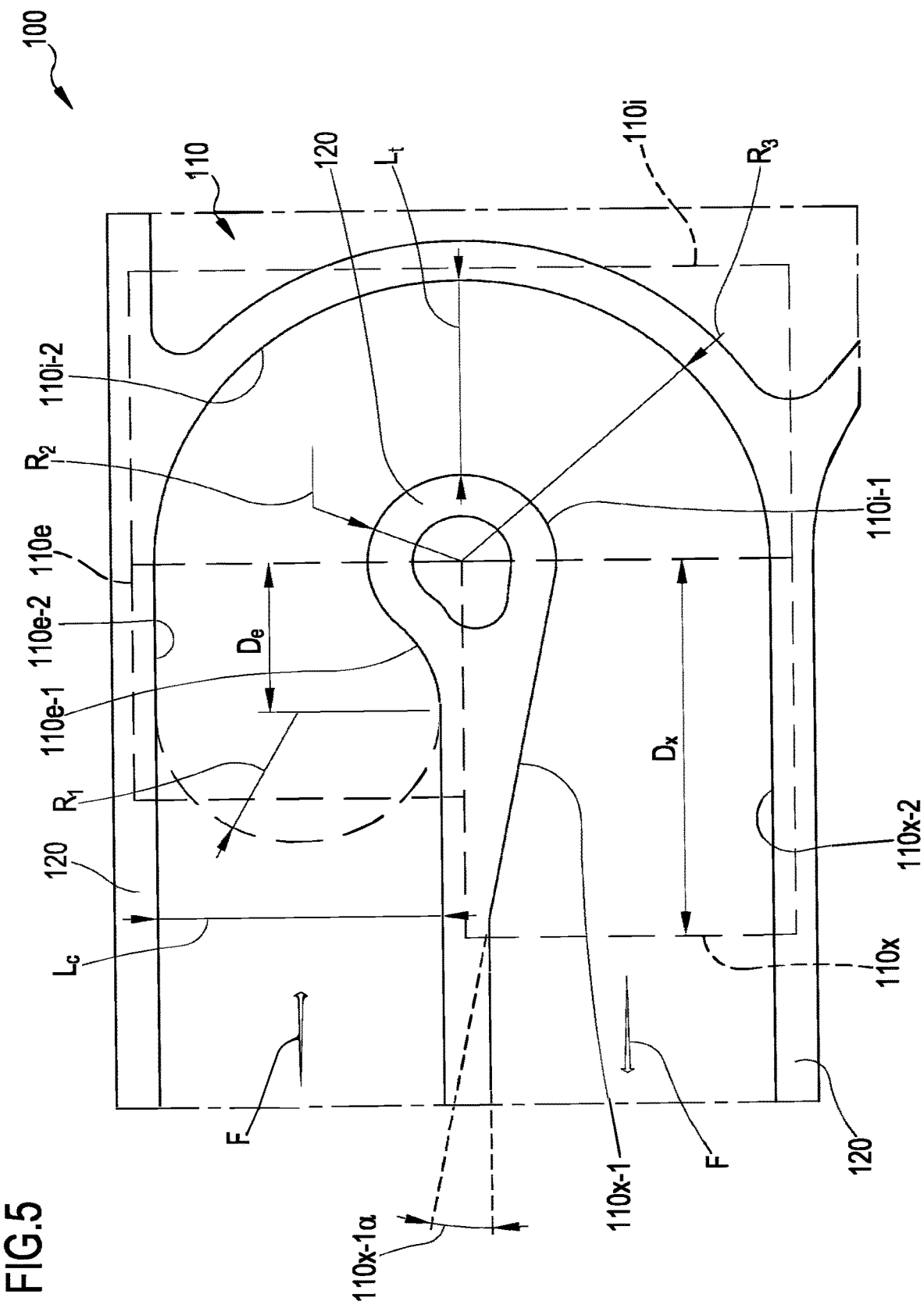
FIG. 5 shows a deflection section of one or more deflection sections as used in a bag for an apparatus for warming fluids, the bag being in accordance with a second embodiment of the present invention.
Figure 8B:
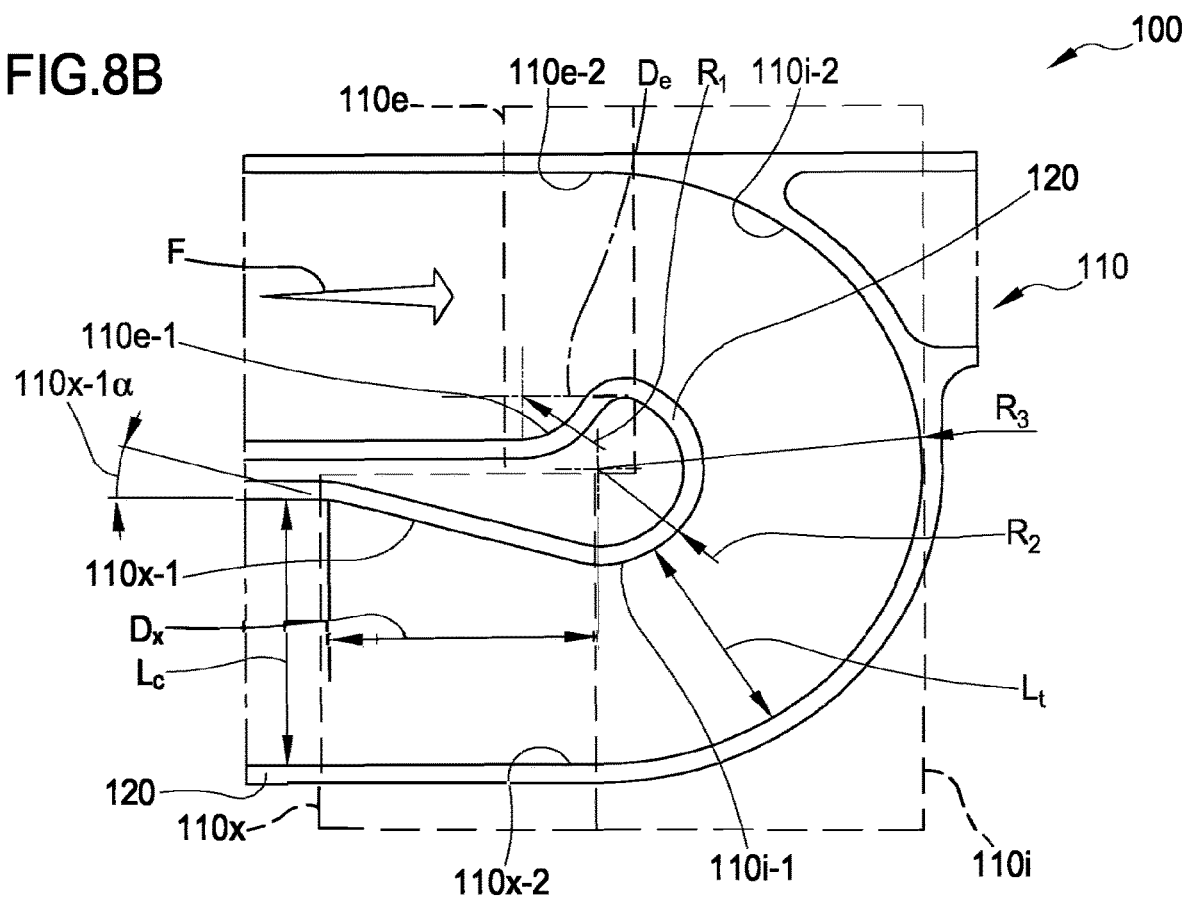
FIGS. 8B and 8C shows details of the bag embodiment of FIG. 8A.
Figure 8C:
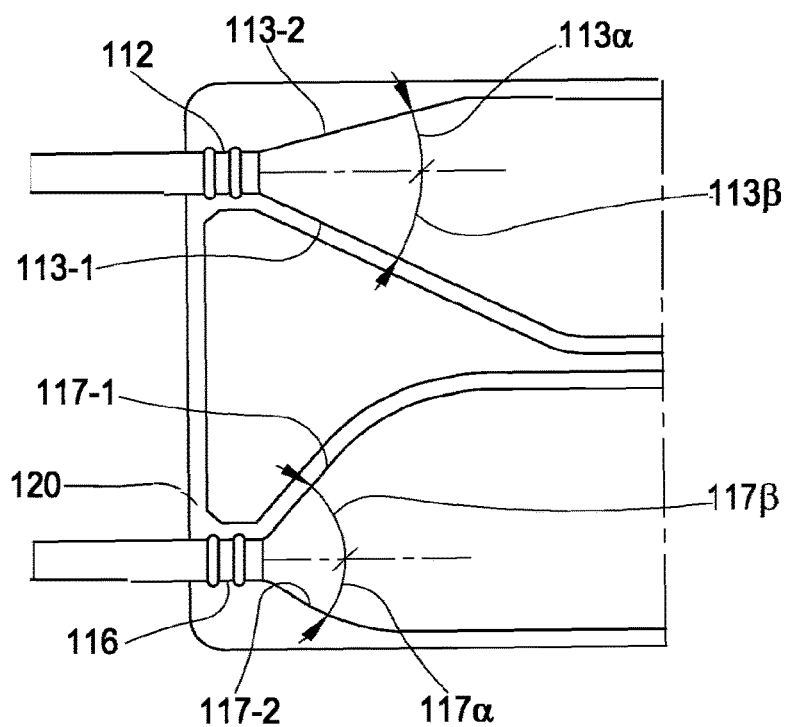

FIG. 5 and corresponding FIG. 8B show a respective deflection section 110 of one or more deflection sections 110 as used in a bag 100 for an apparatus for warming fluids 300 as described above, the bag 100 being in accordance with an embodiment of the present invention. FIGS. 5 and 8B illustrates possible measurements for different elements of the conduit. It is noted, however, that the measurements shown are exemplary and not intended to limit the embodiments described herein.

Welding lines 120 typically have a width of about 2 mm to about 4 mm, particularly about 3 mm. The conduit according to FIGS. 4 and 5 typically has a width of about 20 mm along the connection sections 102. As described with respect to FIG. 4 above, entry sections 110e of deflection sections 110 typically reduce the width of the conduit from about 20 mm to about 15 mm in the intermediate sections 110i. To this aim, entry sections 110e may have an inner edge 110e-1 corresponding to a segment of a circle having a radius of e.g. about 10 mm (see FIG. 5—$R_1$). The circle segment of the inner edge 110e-1 of the entry section 110e then continues into the inner edge 110i-1 of the intermediate section 110i, which is defined by a segment of a circle having a radius $R_2$ of e.g. about 4–5 mm (see FIG. 5). The intermediate section 110i has a width of about 15 mm (see above) and the outer edge 110i-2 thereof is defined by a radius $R_3$ of e.g. about 21.5 mm (see FIG. 5). The exit section 110x has a length in direction of fluid flow F of about 30 mm and is defined by an outer edge 110x-2 continuing tangentially from the outer edge of the intermediate section 110i and an inner edge 110x-1 positioned at an angle 110x-1α of e.g. about 10.26° with respect to a main development axis of the following connection section 102 (e.g. an inner/outer edge thereof). In both the first and second embodiments, the outlet diverging angle, that is the angle between the inner edge 110x-1 and the corresponding edge of the connection section 102, is less than 25°, particularly less than 15°.

FIG. 5 illustrates the asymmetrical configuration of a deflection section 110 according to embodiments of the present invention, as well as the welding lines 120 providing bag 100 with a conduit of the corresponding shape.

The conduit according to FIGS. 8A to 8C typically has a width of about 40 mm along the connection sections 102. As described, entry sections 110e of deflection sections 110 typically reduce the width of the conduit from about 40 mm to about 30 mm in the intermediate sections 110i. To this aim, entry sections 110e may have an inner edge 110e-1 corresponding to a segment of a circle having a radius of e.g. about 10 mm (see FIG. 5, $R_1$). The circle segment of the inner edge 110e-1 of the entry section 110e then continues into the inner edge 110i-1 of the intermediate section 110i, which is defined by a segment of a circle having a radius of e.g. about 6.5 mm (see FIG. 5, $R_2$). The intermediate section 110i has a width of about 30 mm (see above) and the outer edge 110i-2 thereof is defined by a radius of e.g. about 44.5 mm (see FIG. 5, $R_3$). The exit section 110x has a length in direction of fluid flow F of about 40 mm and is defined by an outer edge 110x-1 continuing tangentially from the outer edge of the intermediate section 110i and an inner edge 110x-2 positioned at an angle 110x-1α of e.g. about 14° with respect to a main development axis of the following connection section 102 (e.g. an inner/outer edge thereof). In both the first and second embodiments, the outlet diverging angle, that is the angle between the inner edge 110x-2 and the corresponding edge of the connection section 102, is less than 25°, particularly less than 15°.

Figure 6B:
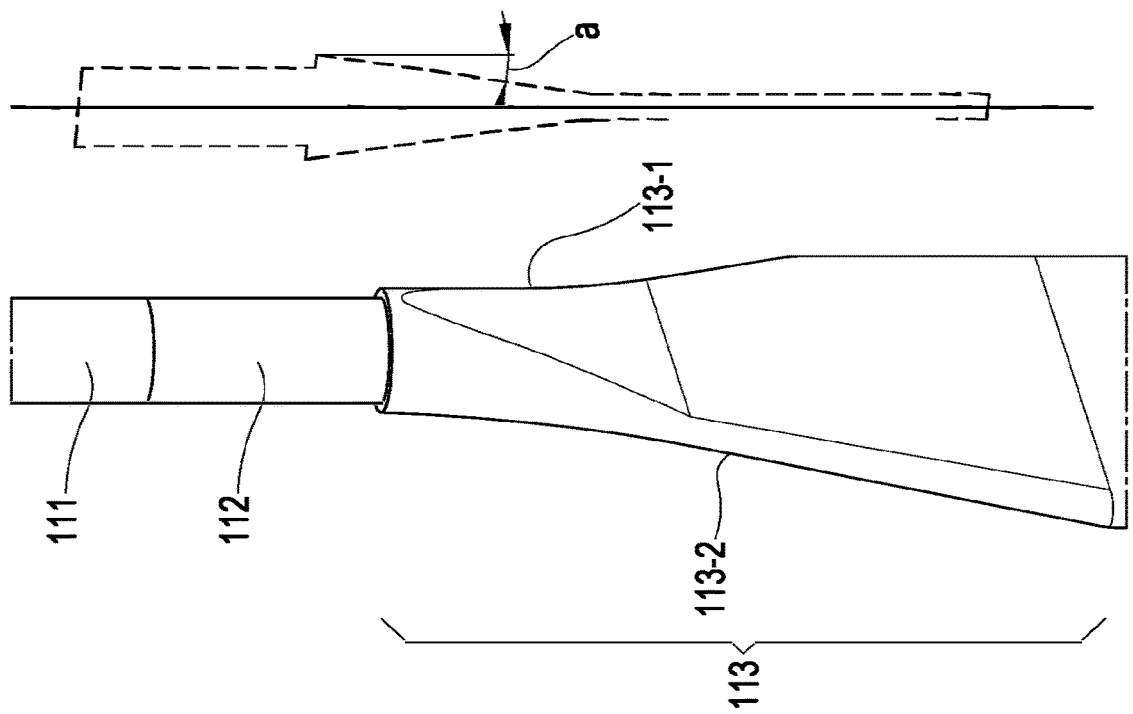
FIG. 6B shows a perspective view of an inlet section in accordance with embodiments of the present invention.
Figure 6A:
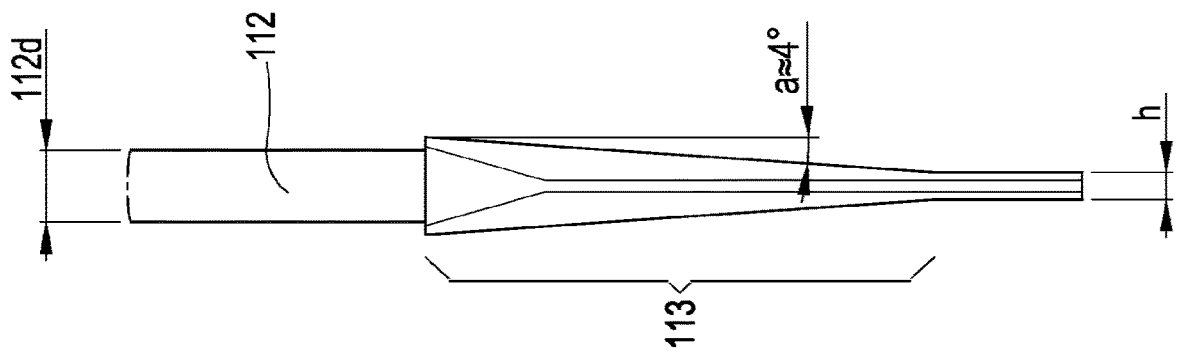
FIG. 6A shows a side view of an inlet section in accordance with embodiments of the present invention.

FIG. 6A shows a side view of an inlet section 113 in accordance with embodiments of the present invention. FIG. 6A illustrates a key parameter in transitioning the diameter 112d of the inlet port 112 (or directly of the tubing 111) to the height h of the connection sections 102, namely parameter a describing an angle between a plane parallel to a longitudinal extension of connection sections 102 and a connecting section adjacent to the inlet port 112 or the tubing 111. Due to the diameter of the tubing 111 or of the inlet port 112 being larger than the height h of the connection sections 102, the two opposite layers defining the sides of the inlet section have an angular configuration in which angle 'a' determines over which distance, in direction of fluid flow F, the substantially circular diameter 112*d* of the inlet port 112 or tubing 111 is adapted to the substantially flat cross section of the connection sections 102 (e.g., having a height h much smaller than the maximum width $L_c$). FIG. 6A illustrates an angle 'a' of about 4°, resulting in the substantially circular diameter 112*d* of the inlet port 112 being adapted slowly (e.g., over substantially the entire inlet section 113) to the substantially flat cross section of the connection sections 102 (un-pinched situation).

FIG. 6B shows a perspective view of an inlet section 113 in accordance with embodiments of the present invention. FIG. 6B illustrates an angle 'a' of about 10°, resulting in the substantially circular diameter 112*d* of the inlet port 112 being adapted more quickly than as shown in FIG. 6A (e.g. over a shorter section inlet section 113) to the substantially flat cross section of the connection sections 102. In other terms, FIG. 6B shows a situation in which the inlet section is pinched in correspondence of the second portion 113-2 where the two surfaces become parallel. As can be seen from FIGS. 6A and 6B, the corresponding sections of the inlet section 113 (or portions thereof) depend on the value of the angle 'a' and, thus, do not have to be limited to an extension of the inlet section 113 itself. FIG. 6B shows that the inlet section 113 has one portion 113-1 in which opposing layers of material are at an angle 'a' with respect to a plane parallel to the connection sections 102 (not shown) and another portion 113-2 in which the opposing layers are substantially parallel and at a distance substantially corresponding to the height h of the connection sections 102.

Generally, the angle 'a' may be modified to determine the manner in which fluid entering the container 100 at the inlet port 112 is being spread laterally to conform to the substantially flat cross section of the connection sections 102. Here, a larger angle 'a' may lead to the fluid being spread laterally more quickly or effectively (e.g. along a shorter distance in direction of fluid flow F) in order to reduce or eliminate the formation of regions A of fluid flow having a relatively lower velocity.

Figure 7D:
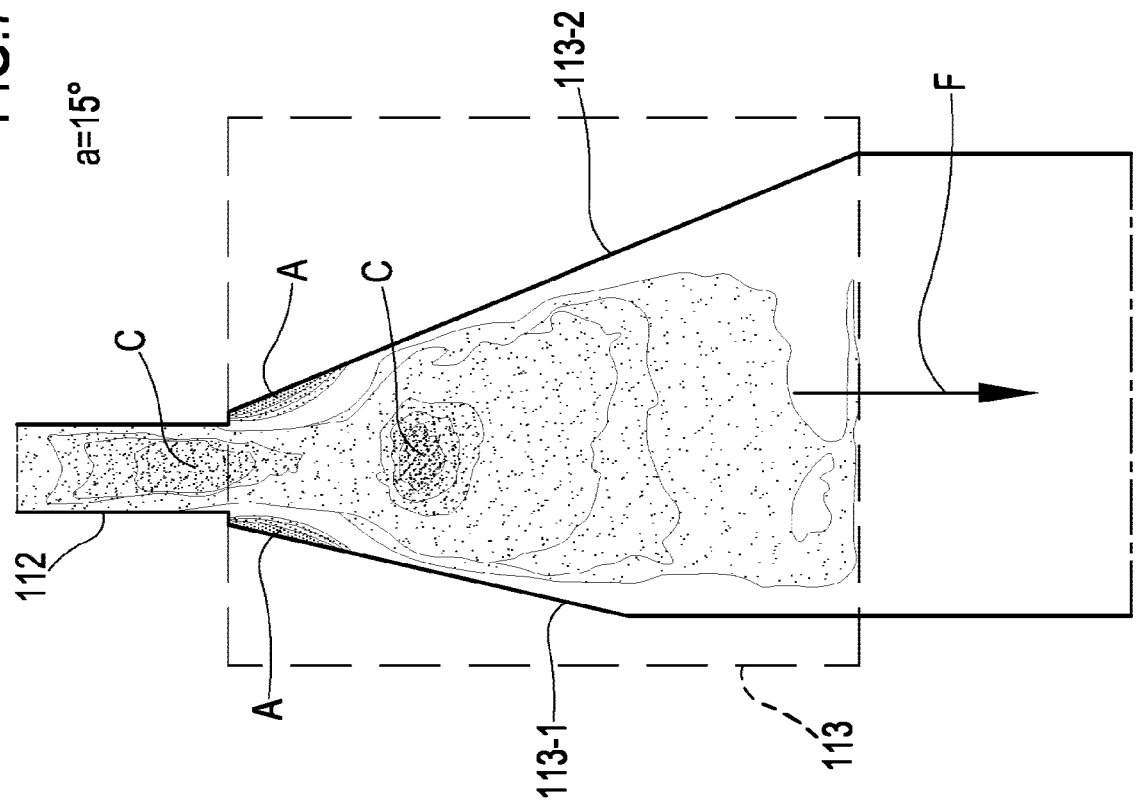
Figure 7C:
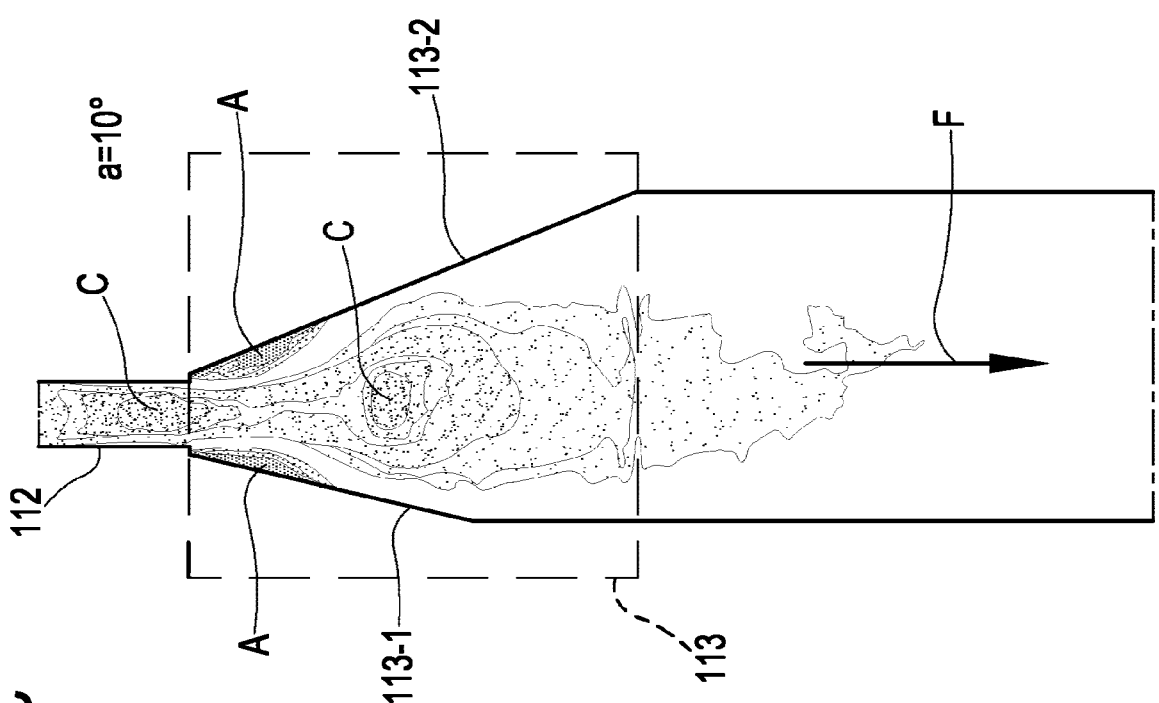

FIGS. 7A to 7D show fluid flow based on different alternative embodiments of inlet sections in accordance with embodiments of the present invention. FIGS. 7A to 7D illustrate the influence of the angle 'a' on the fluid dynamics and, in particular, on the formation of regions A and C indicating regions of fluid flow having respectively relatively lower and higher velocity (e.g. contours of the velocity magnitude). FIG. 7A shows a fluid flow simulation for angle 'a'=4°, FIG. 7B shows a fluid flow simulation for angle 'a'=5°, FIG. 7C shows a fluid flow simulation for angle 'a'=10°, and FIG. 7D shows a fluid flow simulation for angle 'a'=15°. As can be seen, each angle a and each associated configuration of the respective inlet section 113 influences the fluid flow through the inlet section and, in particular, the formation of regions A and C as described above. It is noted that the examples shown in FIGS. 7A to 7D are based on the same fluid having a specific viscosity and being conveyed at the same fluid flow rate for reasons of comparison of different configurations for inlet sections 113. The pressure drop for the examples of FIGS. 7A to 7D was substantially the same with 3133 Pa, 3152 Pa, 3182 Pa, and 3208 Pa, respectively.

While the invention has been described in connection with what is presently considered to be the most practical embodiment, it is to be understood that the invention is not to be limited to the disclosed embodiment, but on the contrary, is intended to cover various modifications and equivalent arrangements included within the spirit and the scope of the appended claims.

The invention claimed is:

1. A container for enabling fluid flow, wherein the container comprises a flexible bag with at least a first and a second film sealed to one another, the container further comprising:
   an inlet port;
   an outlet port; and
   a fluid conduit to put the inlet port in fluid communication with the outlet port, the fluid conduit comprising
      one or more deflection sections,
      a connection section located upstream from at least one of the one or more deflection sections, and
      a successive connection section located downstream from the at least one or more deflection sections,
   wherein the fluid conduit has a maximum width in a direction of the fluid flow through the fluid conduit,
   wherein at least one of the one or more deflection sections further comprises an entry section and an exit section, each respective exit section being arranged downstream, in the direction of the fluid flow, from each respective entry section,
   wherein the entry section includes an inner edge having a nonlinear shape with a concave curve trend in a first portion and a convex curve trend in a second portion and an outer edge having a linear shape, wherein the outer edge contacts and continues straight from an outer edge of the connection section,
   wherein a width of the fluid conduit decreases along the direction of the fluid flow through the entry section over a first distance, from the maximum width to a narrower width, wherein a decrease through the entry section is non-uniform along the direction of the fluid flow through the entry section,
   wherein the exit section includes an inner edge having a linear shape corresponding to a line segment positioned at an angle with respect to an outer edge of the exit section, wherein the outer edge of the exit section contacts and continues straight from an outer edge of the successive connection section, and
   wherein the width of the fluid conduit increases along the direction of the fluid flow through the exit section over a second distance, from the narrower width to the maximum width.

2. The container according to claim 1, wherein, for each of the one or more deflection sections, the entry section has a first end and a second end, the first end of the entry section being upstream, in the direction of the fluid flow, of the second end of the entry section,
   wherein the exit section has a first end and a second end, the first end of the exit section being upstream, in the direction of the fluid flow, of the second end of the exit section, and
   wherein the width of the fluid conduit at the first end of the entry section is equal to the width of the fluid conduit at the second end of the exit section.

3. The container according to claim 2, wherein $$0.5 \leq \frac{L_t}{L_c} \leq 0.85,$$

and wherein $L_t$ is a width of an intermediate section located between the entry and exit sections and $L_c$ is the maximum width.

4. The container according to claim 1, wherein the width of the fluid conduit decreases along the direction of the fluid flow through the entry section according to a first radius of curvature in the first portion of the entry section and according to a second radius of curvature in the second portion of the entry section.

5. The container according to claim 4, wherein the second radius of the curvature in the second portion of the entry section is $R_2$ and the maximum width is $L_c$, wherein a ratio $R_2/L_c$ ranges from 0.15 to 0.50.

6. The container according to claim 4, wherein the second radius of the curvature in the second portion of the entry section is $R_2$ and the maximum width is $L_c$, wherein a ratio $R_2/L_c$ is less than 0.3.

7. The container according to claim 4, wherein the first radius of the curvature in the first portion of the entry section is $R_1$ and the maximum width is $L_c$, wherein a ratio $R_1/L_c$ ranges from 0.24 to 0.55.

8. The container according to claim 4, wherein the first distance is smaller than the second distance and the first radius of curvature is different than the second radius of curvature.

9. The container according to claim 1, wherein a decrease in the first portion and a decrease in the second portion are different from one another, and wherein the width of the fluid conduit decreases along the direction of the fluid flow through the entry section less than linearly in the first portion and more than linearly in the second portion.

10. The container according to claim 1, wherein each of the one or more deflection sections further comprises an intermediate section interposed between the entry section and the exit section,
wherein each respective intermediate section:
has a constant width equal to the narrower width,
is directly adjacent to the corresponding entry section, the corresponding entry section being a direct extension of the respective intermediate section, and
is directly adjacent to the corresponding exit section, the corresponding exit section being a direct extension of the respective intermediate section,
wherein the fluid conduit is provided with an inner radius $R_2$ calculated as $$R_2 = \left(1 - \frac{L_t}{L_c}\right) \cdot L_c + \frac{\text{weld}}{2},$$

with $L_c$=the maximum width, $L_t$=the width of the intermediate section, and weld=width of a weld, and
wherein the fluid conduit is provided with an outer radius $R_3$, wherein $$R_3 = L_c + \frac{\text{weld}}{2}.$$

11. The container according to claim 10, wherein the intermediate section has an inner edge and an opposite outer edge, the inner edge having a radius smaller than a radius of the outer edge, and wherein each of the entry section and the exit section has a respective inner edge in extension to the inner edge of the intermediate section and wherein each of the entry section and the exit section has a respective outer edge in extension to the outer edge of the intermediate section,
wherein the width of the fluid conduit decreases along the direction of the fluid flow through the entry section due to a directional change of the inner edge of the entry section, the outer edge of the entry section continuing straight or tangentially in extension from the outer edge of the intermediate section, and
wherein the width of the fluid conduit increases along the direction of the fluid flow through the exit section due to a directional change of the inner edge of the exit section, the outer edge of the exit section continuing straight or tangentially in extension from the outer edge of the intermediate section.

12. The container according to claim 1, wherein the width of the fluid conduit decreases along the direction of the fluid flow through the entry section due to a directional change of the inner edge of the entry section, and
wherein the width of the fluid conduit increases along the direction of the fluid flow through the exit section due to a directional change of the inner edge of the exit section, wherein the outer edge of the exit section is straight.

13. The container according to claim 1, wherein the fluid conduit further comprises a plurality of connection sections in addition to the connection section and the successive connection section,
wherein, along each of the plurality of connection sections, the width is constant, wherein the fluid conduit along each of the plurality of connection sections is straight, and
wherein the plurality of connection sections comprises an inlet section connected to the inlet port and to an adjacent first connection section of the plurality of connection sections, the inlet section providing the fluid conduit with a transition from a diameter of the inlet port to the maximum width of the fluid conduit at the first connection section.

14. The container according to claim 13, wherein the inlet section includes an inner edge and an outer edge, the inner edge and the outer edge each forming a respective inlet angle with respect to an axis of the inlet port of 5° to 30°.

15. The container according to claim 13, wherein the plurality of connection sections comprises an outlet section connected to the outlet port and to an adjacent second connection section of the plurality of connection sections, the outlet section providing the fluid conduit with a transition from a diameter of the outlet port to the maximum width of the fluid conduit at the second connection section, the outlet section including an inner edge and an outer edge, the inner edge and the outer edge each forming a respective outlet angle with respect to an axis of the outlet port of 25° to 60°.

16. The container according to claim 1, further comprising a proximal end and a distal end opposite the proximal end, wherein both the inlet port and the outlet port are arranged at the proximal end, wherein the one or more deflection sections includes a number of deflection sections, the number of deflection sections being uneven, wherein the number of deflection sections is equal to 3, 5, 7, or 9.

17. The container according to claim 1, wherein the inlet port is configured for connecting to a fluid inlet line of a blood treatment apparatus and for receiving medical fluid from the fluid inlet line through the inlet port, wherein the outlet port is configured for connecting to a fluid outlet line of the blood treatment apparatus and for releasing the medical fluid from the outlet port into the fluid outlet line.

18. The container according to claim 1, wherein a ratio between the maximum width of the fluid conduit over a maximum height of the fluid conduit is greater than 10.

19. A container for enabling fluid flow, wherein the container comprises a flexible bag with at least a first and a second film sealed to one another, the container further comprising:
- an inlet port;
- an outlet port; and
- a fluid conduit to put the inlet port in fluid communication with the outlet port, the fluid conduit comprising
  - one or more deflection sections,
  - a connection section located upstream from at least one of the one or more deflection sections, and
  - a successive connection section located downstream from the at least one or more deflection sections, wherein the fluid conduit has a maximum width in a direction of the fluid flow through the fluid conduit,
- wherein at least one of the one or more deflection sections further comprises an entry section and an exit section, each respective exit section being arranged downstream, in the direction of the fluid flow, from each respective entry section,
- wherein, for each of the one or more deflection sections
  - the entry section has a first end and a second end, the first end of the entry section being upstream, in the direction of the fluid flow, of the second end of the entry section,
  - the entry section includes an inner edge having a nonlinear shape with a concave curve trend in a first portion and a convex curve trend in a second portion and an outer edge having a linear shape, wherein the outer edge contacts and continues straight from an outer edge of the connection section,
  - the exit section has a first end and a second end, the first end of the exit section being upstream, in the direction of the fluid flow, of the second end of the exit section, wherein the exit section includes an inner edge having a linear shape corresponding to a line segment positioned at an angle with respect to an outer edge of the exit section, wherein the outer edge of the exit section contacts and continues straight from an outer edge of the successive connection section in the direction of the fluid flow, and
  - an intermediate section interposed between the entry section and the exit section, the intermediate section having a constant width, the intermediate section being provided with a deflection of about 180°,
- wherein a width of the fluid conduit decreases along the direction of the fluid flow through the entry section over a first distance from the maximum width to a narrower width and the width of the fluid conduit increases constantly along the direction of the fluid flow through the exit section over a second distance from the narrower width to the maximum width,
- wherein the width of the fluid conduit at the first end of the entry section is equal to the width of the fluid conduit at the second end of the exit section and the constant width of the intermediate section is equal to the narrower width, the first distance being smaller than the second distance, wherein $$0.5 \leq \frac{L_t}{L_c} \leq 0.85,$$

and
wherein $L_t$ is the constant width of the intermediate section located between the entry and exit sections and $L_c$ is the maximum width.

20. A container for enabling fluid flow, wherein the container comprises a flexible bag with at least a first and a second film sealed to one another, the container further comprising:
- an inlet port;
- an external inlet tubing having a section diameter and being connected to the inlet port;
- an outlet port; and
- a fluid conduit configured for putting the inlet port in fluid communication with the outlet port, the fluid conduit comprising
  - one or more deflection sections,
  - a connection section located upstream from at least one of the one or more deflection sections, and
  - a successive connection section located downstream from the at least one or more deflection sections,
- wherein the fluid conduit has a maximum width in a direction of the fluid flow through the fluid conduit and a conduit height, the section diameter of the inlet tubing being larger than the conduit height,
- wherein at least one of the one or more deflection sections further comprises an entry section and an exit section, each respective exit section being arranged downstream, in the direction of the fluid flow, from each respective entry section,
- wherein the entry section includes an inner edge having a nonlinear shape and an outer edge having a linear shape, wherein the outer edge contacts and continues straight from an outer edge of the connection section,
- wherein an inlet section fluidly connects the inlet tubing with the fluid conduit,
- wherein the inlet section comprises a first plane and a second plane, opposite to the first plane, developing from the inlet tubing towards the fluid conduit and converging towards the fluid conduit, and
- wherein the exit section includes an inner edge having a linear shape corresponding to a line segment positioned at an angle with respect to an outer edge of the exit section, the outer edge of the exit section contacting and continuing straight from an outer edge of the successive connection section in the direction of the fluid flow.

21. The container according to claim 20, wherein the first plane and/or the second plane of the inlet section defines an angle with respect to a longitudinal extension of a fluid conduit main plane less than 20°.

22. The container according to claim 20, wherein the inlet section further includes a terminal portion connecting the first plane and second plane with the fluid conduit, the terminal portion including two respective flat layers substantially parallel placed at a distance corresponding to the conduit height, the first plane and the second plane being connected to the respective flat layers of the terminal portion.

* * * * *